(12) United States Patent
Buehler

(10) Patent No.: US 8,598,207 B2
(45) Date of Patent: Dec. 3, 2013

(54) COMPOSITIONS CONTAINING OPIOID ANTAGONISTS

(75) Inventor: John D. Buehler, Blue Bell, PA (US)

(73) Assignee: Adolor Corporation, Lexington, MA (US)

( * ) Notice: Subject to any disclaimer, the term of this patent is extended or adjusted under 35 U.S.C. 154(b) by 0 days.

(21) Appl. No.: 13/477,742

(22) Filed: May 22, 2012

(65) Prior Publication Data

US 2012/0232114 A1    Sep. 13, 2012

Related U.S. Application Data

(60) Continuation of application No. 12/728,622, filed on Mar. 22, 2010, now abandoned, which is a division of application No. 11/143,535, filed on Jun. 2, 2005, now Pat. No. 7,700,626.

(60) Provisional application No. 60/576,939, filed on Jun. 4, 2004.

(51) Int. Cl.
    *A61K 31/454* (2006.01)
(52) U.S. Cl.
    USPC ........... 514/326; 514/184; 514/619; 514/646; 514/649; 514/656
(58) Field of Classification Search
    USPC ................ 514/331, 184, 326, 619, 646, 656
    See application file for complete search history.

(56) References Cited

U.S. PATENT DOCUMENTS

| | | | |
|---|---|---|---|
| 4,115,400 | A | 9/1978 | Zimmerman |
| 4,581,456 | A | 4/1986 | Barnett |
| 4,871,720 | A | 10/1989 | Jaeggi |
| 4,891,379 | A | 1/1990 | Zimmerman et al. |
| 5,136,040 | A | 8/1992 | Werner |
| 5,159,081 | A | 10/1992 | Cantrell et al. |
| 5,250,542 | A | 10/1993 | Cantrell et al. |
| 5,270,328 | A | 12/1993 | Cantrell et al. |
| 5,434,171 | A | 7/1995 | Frank et al. |
| 6,451,806 | B2 | 9/2002 | Farrar |
| 6,469,030 | B2 | 10/2002 | Farrar et al. |
| 7,700,626 | B2 | 4/2010 | Buehler |
| 2003/0158220 | A1 | 8/2003 | Foss et al. |
| 2010/0240690 | A1 | 9/2010 | Buehler |

FOREIGN PATENT DOCUMENTS

| | | |
|---|---|---|
| EP | 0693280 | 1/1996 |
| EP | 1 308 440 | 5/2003 |
| WO | WO 9534290 | 12/1995 |
| WO | WO 9534293 | 12/1995 |
| WO | WO 9635564 | 11/1996 |
| WO | WO 9635565 | 11/1996 |
| WO | WO 01/37785 | 5/2001 |
| WO | WO 2005/055953 | 6/2005 |

OTHER PUBLICATIONS

*Dorland's Illustrated Medical Dictionary*, p. 816, 27th ed. (W.B. Saunders Company, Philadelphia 1988).
*Dorland's Illustrated Medical Dictionary*, p. 375, 27th ed. (W.B. Saunders Company, Philadelphia 1988).
Resnick, J., et al., "Delayed gastric emptying and postoperative Ileus after nogastric abdominal surgery: Part I," *Am. J. of Gastroenterology*, 1997, 92(5), 751-762.
Resnick, J., et al., "Delayed gastric emptying and postoperative Ileus after nogastric abdominal surgery: Part I," *Am. J. of Gastroenterology*, 1997, 92(6), 934-940.
Livingston, E.H., et al., "Postoperative Ileus,", *Digestive Diseases and Sciences*, 1990, 35(1), 121-132.
Orchin, et al, *The Vocabulary of Organic Chemistry*, John Wiley and Sons, Inc., pp. 126-127.
*Handbook of Pharmaceutical Excipients*, 3rd Ed. Washington, D.C: American Pharmaceutical Association, 1998.
*Physicians' Desk Reference*, 2004.
*Physicians' Desk Reference*, 2005, 201-215.
Mao, M.J. et al, "Oral administration of dextromethorphan prevents the development of morphine tolerance and dependence in rats,"*Pain* 3120, 1996, 67, 361-368.
Dourish, C.T. et al, "Enhancement of morphine analgesia and prevention of morphine tolerance in the rat by the cholecystokinin antagonist L-364, 718," *Eur. J. Pharmacol.*, 1988, 147, 469-472.
Bhargava, H.N. et al, "Effect of nitric oxide synthase inhibition on tolerance to the analgesic action of D-Pen$^2$, DPen$^5$ enkephanlin and morphine in the mouse," *Neuropeptides*, 1996, 30(3), 219-223.
Bilsky, E.J. et al, "Effects of naloxone and D-Phe-Cys-Tyr-D-Trp-Arg-Thr-Pen-Thr-NH2 and the protein kinase inhibitors H7 and H8 on acute morphine dependence and antinociceptive tolerance in mice," *J. Pharmacol. Exp. Ther.* 1996, 277(1), 484-490.
Nichols, M.L. et al, "Enhancement of the antiallodynic and antinociceptive efficacy of spinal morphine by antisera to dynorphin A (1-13) or MK-801 in a nerve-ligation model of peripheral neuropathy," *Pain*, 1997, 69, 317-322.
Greene, T.W., et al., *Protective Groups in Organic Sythesis* 2nd Ed., Wiley & Sons, 1991, Chapter 2 (pp. 1-142); Chapter 4(pp. 175-223); Chapter 5(pp. 224-276) ; Chapter 7(pp. 309-405).

(Continued)

*Primary Examiner* — Renee Claytor
*Assistant Examiner* — Sahar Javanmard
(74) *Attorney, Agent, or Firm* — Dechert LLP

(57) ABSTRACT

Compositions containing opioid antagonists, particularly alvimopan and its active metabolite, with improved solubility and bioavailability for oral or parenteral administration, injectable dosage formulations, kits, and methods of making and using same are disclosed. In preferred embodiments, invention provides injectable formulations containing opioid antagonists, particularly alvimopan and its active metabolite, having low solubility that may be readily prepared, are stable during storage, and provide maximum levels of opioid antagonists when administered parenterally, particularly via injection. The results are achieved by a combination of processing techniques and component selection.

17 Claims, No Drawings

(56) References Cited

OTHER PUBLICATIONS

Werner, J.A., et al, "Synthesis of trans-3,4-(3-hydroxyphenyl)piperidine opioid antagonists: application of the Cis-thermal elimination of carbonates to alkaloid synthesis," *Journal of organic Chemistry*, 61, 587-597 (1996).

*Remington's Pharmaceutical Sciences*, Mack Publishing Co., 1980, Chapters 83-92, 1519-1712.

Jennings, Medical Device Link, 1997; http://www.devicelink.com/grabber.php3?URL=http://www.devicelink.com/ivdt/archive/97/01/006.html.

Supplementary European Search Report completed Oct. 30, 2009 for EP05757306.

COMPOSITIONS CONTAINING OPIOID ANTAGONISTS

CROSS-REFERENCE TO RELATED APPLICATIONS

This application is a continuation of U.S. application Ser. No. 12/728,622, filed Mar. 22, 2010, which is a divisional of U.S. patent application Ser. No. 11/143,535, filed Jun. 2, 2005, now U.S. Pat. No. 7,700,626, issued Apr. 20, 2010, which claims benefit under 35 USC 119(e) of U.S. Provisional Application No. 60/576,939, filed Jun. 4, 2004. The disclosures of each of the above-identified applications are incorporated herein by reference in their entireties.

FIELD OF THE INVENTION

The present invention relates to compositions containing opioid antagonists. More particularly, the present invention relates to compositions containing opioid antagonists, injectable dosage formulations, kits, and methods of preparing and using same.

BACKGROUND OF THE INVENTION

Oral dosage forms, such as tablets and capsules, of pharmaceuticals are widely used dosage forms. However, certain patients are unable to tolerate oral dosage forms due to their inability to swallow the tablet or capsule, due to age, infirmity, or lack of consciousness. Thus, it would be desirable to be able to administer the pharmaceutical via a parenteral route, such as intravenous, intramuscular, or subcutaneous injection. Formulating solid pharmaceuticals for administration via parenteral routes can be problematic, however, because of the frequent difficulty of solubilizing the solid active ingredient in a pharmaceutically acceptable liquid solvent.

The low solubility problem has been addressed in the following ways:
1. Solubilizing surfactants may be used to increase the solubility of the active ingredient in the solvent. Unfortunately, the solubilizing surfactants may cause anaphylactic reactions in susceptible patients.
2. Oil-in-water emulsions may be used but such formulations suffer from a number of drawbacks, including pain at the injection site, poor physical stability, potential for embolisms, and the need for strict aseptic handling.
3. Complexing the active ingredients with amphipathic agents that increase their solubility (such as β-cyclodextrin) may be used, but these suffer limitations including higher cost and their currently limited acceptance by regulatory agencies for use in human pharmaceutical products.

[[2(S)-[[4(R)-(3-hydroxyphenyl)-3(R),4-dimethyl-piperidinyl]methyl]-1-oxo-3-phenylpropyl]amino]acetic acid dihydrate (USAN name alvimopan) and its active metabolite are peripherally-acting μ opioid antagonists that may be used in the treatment of postoperative ileus, postpartum ileus, pruritis, constipation, opioid bowel dysfunction, urinary retention, biliary spasm, opioid bowel dysfunction, colic, postoperative nausea, and/or postoperative vomiting as well as other indications. Alvimopan is currently available in solid dosage form. However, it would be desirable to provide the active ingredient in an injectable form to avoid the problems with swallowing tablets or capsules or in administering to patients who are undergoing surgery and not conscious. Alvimopan and its active metabolite are 3,4-disubstituted-4-aryl piperidines that are zwitterions. They have extremely low solubility in water and many common pharmaceutically acceptable solvents.

What would be desirable are injectable dosage formulations of alvimopan and related 4-aryl substituted piperidine compounds that are zwitterionic in nature. The present invention is directed to these and other important objectives.

SUMMARY OF THE INVENTION

In one embodiment, the present invention is directed to methods, comprising the steps of:
a. providing a composition, comprising:
  (i) a pharmaceutically-acceptable metal salt of at least one compound of formula I:

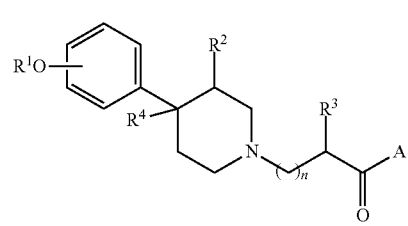

wherein:
$R^1$ is hydrogen or alkyl;
$R^2$ is hydrogen, alkyl or alkenyl;
$R^3$ is hydrogen, alkyl, alkenyl, aryl, cycloalkyl, cycloalkenyl, cycloalkyl-substituted alkyl, cycloalkenyl-substituted alkyl or aralkyl;
$R^4$ is hydrogen, alkyl or alkenyl;
A is $OR^5$ or $NR^6R^7$;
$R^5$ is hydrogen, alkyl, alkenyl, cycloalkyl, cycloalkenyl, cycloalkyl-substituted alkyl, cycloalkenyl-substituted alkyl, or aralkyl;
$R^6$ is hydrogen or alkyl;
$R^7$ is hydrogen, alkyl, alkenyl, cycloalkyl, aryl, cycloalkyl-substituted alkyl, cycloalkenyl, cycloalkenyl-substituted alkyl, aralkyl, aralkyl, or alkylene substituted B or, together with the nitrogen atom to which they are attached, $R^6$ and $R^7$ form a heterocyclic ring;
B is

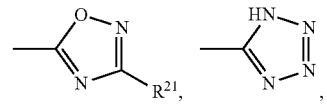

$C(=O)W$ or $NR^8R^9$;
$R^8$ is hydrogen or alkyl;
$R^9$ is hydrogen, alkyl, alkenyl, cycloalkyl-substituted alkyl, cycloalkyl, cycloalkenyl, cycloalkenyl-substituted alkyl, aryl or aralkyl or, together with the nitrogen atom to which they are attached, $R^8$ and $R^9$ form a heterocyclic ring;
W is $OR^{10}$, $NR^{11}R^{12}$, or OE;
$R^{10}$ is hydrogen, alkyl, alkenyl, cycloalkyl, cycloalkenyl, cycloalkyl-substituted alkyl, cycloalkenyl-substituted alkyl, or aralkyl;
$R^{11}$ is hydrogen or alkyl;

R¹² is hydrogen, alkyl, alkenyl, aryl, cycloalkyl, cycloalkenyl, cycloalkyl-substituted alkyl, cycloalkenyl-substituted alkyl, aralkyl or alkylene substituted C(=O)Y or, together with the nitrogen atom to which they are attached, R¹¹ and R¹² form a heterocyclic ring;

E is

[structure: 2-oxo-1,3-dioxol-4-yl with CH₂— and CH₃ substituents]

alkylene substituted (C=O)D, or —R¹³OC(=O)R¹⁴;
$R^{13}$ is alkyl substituted alkylene;
$R^{14}$ is alkyl;
D is $OR^{15}$ or $NR^{16}R^{17}$;
$R^{15}$ is hydrogen, alkyl, alkenyl, cycloalkyl, cycloalkenyl, cycloalkyl-substituted alkyl, cycloalkenyl-substituted alkyl, or aralkyl;
$R^{16}$ is hydrogen, alkyl, alkenyl, aryl, aralkyl, cycloalkyl, cycloalkenyl, cycloalkyl-substituted alkyl or cycloalkenyl-substituted alkyl;
$R^{17}$ is hydrogen or alkyl or, together with the nitrogen atom to which they are attached, $R^{16}$ and $R^{17}$ form a heterocyclic ring;
Y is $OR^{18}$ or $NR^{19}R^{20}$;
$R^{18}$ is hydrogen, alkyl, alkenyl, cycloalkyl, cycloalkenyl, cycloalkyl-substituted alkyl, cycloalkenyl-substituted alkyl, or aralkyl;
$R^{19}$ is hydrogen or alkyl;
$R^{20}$ is hydrogen, alkyl, alkenyl, aryl, cycloalkyl, cycloalkenyl, cycloalkyl-substituted alkyl, cycloalkenyl-substituted alkyl, or aralkyl or, together with the nitrogen atom to which they are attached, $R^{19}$ and $R^{20}$ form a heterocyclic ring;
$R^{21}$ is hydrogen or alkyl; and
n is 0 to 4;
(ii) at least one bulking agent that crystallizes;
(iii) at least one weak base; and
(iv) water;
  wherein said composition has an initial pH of at least about 10.5; and
b. adjusting the pH of said composition to a final pH in the range of about 9 to about 11;
wherein, upon administration to a patient, said composition has improved solubility and bioavailability for oral or parenteral administration.

In another embodiment, the invention is directed, in part, to methods, further comprising the step of drying said composition to remove at least a portion of said water to form a partially or fully dried product.

In yet other embodiments, the invention is directed to methods further comprising the step of reconstituting said dried product by combining therewith a pharmaceutically acceptable solvent to form a solution of said dried product.

In other embodiments, the invention is directed to the products produced by each of the above-described methods.

In further embodiments, the invention is directed to methods of further comprising the step of administering said solution of said dried product to a patient.

In yet further embodiments, the invention is directed to compositions, comprising:
a. a pharmaceutically-acceptable metal salt of at least one compound of formula I:

[structure: formula I — piperidine with $R^1O$-phenyl, $R^2$, $R^4$ substituents and N-(CH₂)ₙ-CH(R³)-C(=O)-A side chain]  I wherein:
$R^1$ is hydrogen or alkyl;
$R^2$ is hydrogen, alkyl, or alkenyl;
$R^3$ is hydrogen, alkyl, alkenyl, aryl, cycloalkyl, cycloalkenyl, cycloalkyl-substituted alkyl, cycloalkenyl-substituted alkyl, or aralkyl;
$R^4$ is hydrogen, alkyl, or alkenyl;
A is $OR^5$ or $NR^6R^7$;
$R^5$ is hydrogen, alkyl, alkenyl, cycloalkyl, cycloalkenyl, cycloalkyl-substituted alkyl, cycloalkenyl-substituted alkyl, or aralkyl;
$R^6$ is hydrogen or alkyl;
$R^7$ is hydrogen, alkyl, alkenyl, cycloalkyl, aryl, cycloalkyl-substituted alkyl, cycloalkenyl, cycloalkenyl-substituted alkyl, aralkyl, aralkyl, or alkylene substituted B or, together with the nitrogen atom to which they are attached, $R^6$ and $R^7$ form a heterocyclic ring;
B is

[structures: oxadiazole with $R^{21}$ substituent, and tetrazole with HN]

C(=O)W or $NR^8R^9$;
$R^8$ is hydrogen or alkyl;
$R^9$ is hydrogen, alkyl, alkenyl, cycloalkyl-substituted alkyl, cycloalkyl, cycloalkenyl, cycloalkenyl-substituted alkyl, aryl or aralkyl or, together with the nitrogen atom to which they are attached, $R^8$ and $R^9$ form a heterocyclic ring;
W is $OR^{10}$, $NR^{11}R^{12}$, or OE;
$R^{10}$ is hydrogen, alkyl, alkenyl, cycloalkyl, cycloalkenyl, cycloalkyl-substituted alkyl, cycloalkenyl-substituted alkyl, or aralkyl;
$R^{11}$ is hydrogen or alkyl;
$R^{12}$ is hydrogen, alkyl, alkenyl, aryl, cycloalkyl, cycloalkenyl, cycloalkyl-substituted alkyl, cycloalkenyl-substituted alkyl, aralkyl or alkylene substituted C(=O)Y or, together with the nitrogen atom to which they are attached, $R^{11}$ and $R^{12}$ form a heterocyclic ring;
E is

[structure: 2-oxo-1,3-dioxol-4-yl with CH₂— and CH₃ substituents]

alkylene substituted (C=O)D, or —R¹³OC(=O)R¹⁴;
$R^{13}$ is alkyl-substituted alkylene;
$R^{14}$ is alkyl;
D is $OR^{15}$ or $NR^{16}R^{17}$;

$R^{15}$ is hydrogen, alkyl, alkenyl, cycloalkyl, cycloalkenyl, cycloalkyl-substituted alkyl, cycloalkenyl-substituted alkyl, or aralkyl;

$R^{16}$ is hydrogen, alkyl, alkenyl, aryl, aralkyl, cycloalkyl, cycloalkenyl, cycloalkyl-substituted alkyl, or cycloalkenyl-substituted alkyl;

$R^{17}$ is hydrogen or alkyl or, together with the nitrogen atom to which they are attached, $R^{16}$ and $R^{17}$ form a heterocyclic ring;

Y is $OR^{18}$ or $NR^{19}R^{20}$;

$R^{18}$ is hydrogen, alkyl, alkenyl, cycloalkyl, cycloalkenyl, cycloalkyl-substituted alkyl, cycloalkenyl-substituted alkyl, or aralkyl;

$R^{19}$ is hydrogen or alkyl;

$R^{20}$ is hydrogen, alkyl, alkenyl, aryl, cycloalkyl, cycloalkenyl, cycloalkyl-substituted alkyl, cycloalkenyl-substituted alkyl, or aralkyl or, together with the nitrogen atom to which they are attached, $R^{19}$ and $R^{20}$ form a heterocyclic ring;

$R^{21}$ is hydrogen or alkyl; and n is 0 to 4;

b. at least one bulking agent that crystallizes;

wherein said composition has a density of less than about 1.0 g/cm$^3$;

wherein, upon administration to a patient, said composition has improved solubility and bioavailability for oral or parenteral administration.

In other embodiments, the invention is directed to compositions, comprising:

a. a pharmaceutically-acceptable metal salt of at least one compound of formula I:

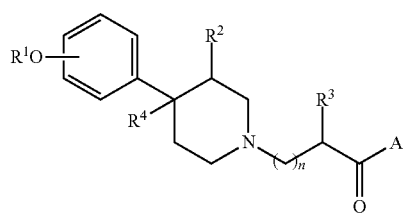

wherein:

$R^1$ is hydrogen or alkyl;

$R^2$ is hydrogen, alkyl or alkenyl;

$R^3$ is hydrogen, alkyl, alkenyl, aryl, cycloalkyl, cycloalkenyl, cycloalkyl-substituted alkyl, cycloalkenyl-substituted alkyl or aralkyl;

$R^4$ is hydrogen, alkyl or alkenyl;

A is $OR^5$ or $NR^6R^7$;

$R^5$ is hydrogen, alkyl, alkenyl, cycloalkyl, cycloalkenyl, cycloalkyl-substituted alkyl, cycloalkenyl-substituted alkyl, or aralkyl;

$R^6$ is hydrogen or alkyl;

$R^7$ is hydrogen, alkyl, alkenyl, cycloalkyl, aryl, cycloalkyl-substituted alkyl, cycloalkenyl, cycloalkenyl-substituted alkyl, aralkyl, aralkyl, or alkylene substituted B or, together with the nitrogen atom to which they are attached, $R^6$ and $R^7$ form a heterocyclic ring;

B is

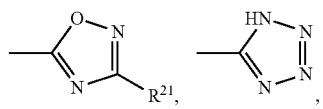

$C(=O)W$ or $NR^8R^9$;

$R^8$ is hydrogen or alkyl;

$R^9$ is hydrogen, alkyl, alkenyl, cycloalkyl-substituted alkyl, cycloalkyl, cycloalkenyl, cycloalkenyl-substituted alkyl, aryl, or aralkyl or, together with the nitrogen atom to which they are attached, $R^8$ and $R^9$ form a heterocyclic ring;

W is $OR^{10}$, $NR^{11}R^{12}$, or OE;

$R^{10}$ is hydrogen, alkyl, alkenyl, cycloalkyl, cycloalkenyl, cycloalkyl-substituted alkyl, cycloalkenyl-substituted alkyl, or aralkyl;

$R^{11}$ is hydrogen or alkyl;

$R^{12}$ is hydrogen, alkyl, alkenyl, aryl, cycloalkyl, cycloalkenyl, cycloalkyl-substituted alkyl, cycloalkenyl-substituted alkyl, aralkyl or alkylene substituted $C(=O)Y$ or, together with the nitrogen atom to which they are attached, $R^{11}$ and $R^{12}$ form a heterocyclic ring;

E is

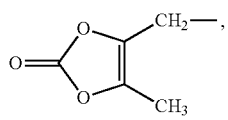

alkylene-substituted $(C=O)D$, or $-R^{13}OC(=O)R^{14}$;

$R^{13}$ is alkyl-substituted alkylene;

$R^{14}$ is alkyl;

D is $OR^{15}$ or $NR^{16}R^{17}$;

$R^{15}$ is hydrogen, alkyl, alkenyl, cycloalkyl, cycloalkenyl, cycloalkyl-substituted alkyl, cycloalkenyl-substituted alkyl, or aralkyl;

$R^{16}$ is hydrogen, alkyl, alkenyl, aryl, aralkyl, cycloalkyl, cycloalkenyl, cycloalkyl-substituted alkyl, or cycloalkenyl-substituted alkyl;

$R^{17}$ is hydrogen or alkyl or, together with the nitrogen atom to which they are attached, $R^{16}$ and $R^{17}$ form a heterocyclic ring;

Y is $OR^{18}$ or $NR^{19}R^{20}$;

$R^{18}$ is hydrogen, alkyl, alkenyl, cycloalkyl, cycloalkenyl, cycloalkyl-substituted alkyl, cycloalkenyl-substituted alkyl, or aralkyl;

$R^{19}$ is hydrogen or alkyl;

$R^{20}$ is hydrogen, alkyl, alkenyl, aryl, cycloalkyl, cycloalkenyl, cycloalkyl-substituted alkyl, cycloalkenyl-substituted alkyl, or aralkyl or, together with the nitrogen atom to which they are attached, $R^{19}$ and $R^{20}$ form a heterocyclic ring;

$R^{21}$ is hydrogen or alkyl; and n is 0 to 4;

b. at least one bulking agent that crystallizes;

c. less than about 1% by weight, based on the total weight of the composition, of a solubilizing surfactant;

d. less than about 10% by weight, based on the total weight of the composition, of a non-aqueous solvent; and e. less than about 500% by weight, based on the total weight of the composition, of cyclodextrin;

wherein, upon administration to a patient, said composition has improved solubility and bioavailability for oral or parenteral administration.

In yet another embodiment, the invention is directed to injectable dosage formulations, comprising the above-described compositions:

In yet other embodiments, the invention is directed to kits, comprising:

a. a container comprising an injectable dosage formulation; and b. instructions for preparing an injectable solution.

In yet other embodiments, the invention is directed to methods of preventing or treating a side effect associated with an opioid in a patient, comprising the step of:

administering to said patient in need thereof an effective amount of the above-described composition.

The methods are useful in the prevention and treatment of ileus, pruritis, constipation, urinary retention, biliary spasm, opioid bowel dysfunction, colic, nausea, or vomiting or combinations thereof, particularly postoperative ileus, postpartum ileus, opioid bowel dysfunction, postoperative nausea, or postoperative vomiting or combinations thereof.

In other embodiments, the invention is directed to methods of preventing or treating pain in a patient, comprising the step of:

administering to said patient in need thereof an effective amount of the above-described composition.

In preferred embodiments, the composition further comprises at least one opioid.

These and other aspects of the invention will become more apparent from the following detailed description.

DETAILED DESCRIPTION OF THE INVENTION

As employed above and throughout the disclosure, the following terms, unless otherwise indicated, shall be understood to have the following meanings.

As used herein, "composition having improved solubility and bioavailability for oral or parenteral administration" refers to a composition containing at least one opioid antagonist suitable for oral or parenteral administration that has a higher level of solubility and bioavailability relative to a composition prepared from the same active ingredient(s) and bulking agent(s) but having different final physical properties (such as density) due to the process by which the composition was formed, preferably minimizing or eliminating the inclusion of undesirable components, such as solubilizing surfactants, non-aqueous solvents, cyclodextrin, and the like used in the prior art to improve the solubility of the active ingredient.

As used herein, "parenteral administration" refers to the administration of a drug to a patient outside of the intestine and not by way of the alimentary tract. The primary routes of parenteral administration to a mammalian host are intravenous, intramuscular, subcutaneous, intradermal, intraocular, intrasynovial, intracardiac, intraspinal, intra-articular, intrathecal, intra-arterial, transepithelial including transdermal, intraperitoneal, ophthalmic, sublingual and buccal; topically including ophthalmic, dermal, ocular, nasal inhalation via insufflation, aerosol and rectal systemic. The preferred parenteral routes of administration are intravenous, intramuscular, and subcutaneous via injection.

As used herein, "bioavailability" refers to the rate and extent to which a drug or other substance becomes available to the target tissue after administration. In the context of this invention, bioavailability refers to the degree to which the opioid antagonist becomes available to the opioid receptors in the central nervous system or peripheral thereto.

As used herein, "alkyl" refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms, herein referred to as "lower alkyl", being preferred. "Branched" refers to an alkyl group in which a lower alkyl group, such as methyl, ethyl, or propyl, is attached to a linear alkyl chain. In certain preferred embodiments, the alkyl group is a $C_1$-$C_5$ alkyl group, i.e., a branched or linear alkyl group having from 1 to about 5 carbons. In other preferred embodiments, the alkyl group is a $C_1$-$C_3$ alkyl group, i.e., a branched or linear alkyl group having from 1 to about 3 carbons. Exemplary alkyl groups include methyl, ethyl, n-propyl, isopropyl, butyl, isobutyl, sec-butyl, tert-butyl, pentyl, hexyl, heptyl, octyl, nonyl, and decyl. "Lower alkyl" refers to an alkyl group having 1 to about 6 carbon atoms. Preferred alkyl groups include the lower alkyl groups of 1 to about 3 carbons. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "alkylene" refers to a bivalent alkyl radical having the general formula $-(CH_2)_n-$, where n is 1 to 10, and all combinations and subcombinations of ranges therein. The alkylene group may be straight, branched or cyclic. Non-limiting examples include methylene, methylene ($-CH_2-$), ethylene ($-CH_2CH_2-$), propylene ($-(CH_2)_3-$), trimethylene, pentamethylene, and hexamethylene. There may be optionally inserted along the alkylene group one or more oxygen, sulfur or optionally substituted nitrogen atoms, wherein the nitrogen substituent is alkyl as described previously. Alkylene groups can be optionally substituted. The term "lower alkylene" herein refers to those alkylene groups having from about 1 to about 6 carbon atoms. Preferred alkylene groups have from about 1 to about 4 carbons.

As used herein, "alkenyl" refers to a monovalent alkyl radical containing at least one carbon-carbon double bond and having from 2 to about 10 carbon atoms in the chain, and all combinations and subcombinations of ranges therein. Alkenyl groups can be optionally substituted. In certain preferred embodiments, the alkenyl group is a $C_2$-$C_{10}$ alkyl group, i.e., a branched or linear alkenyl group having from 2 to about 10 carbons. In other preferred embodiments, the alkenyl group is a $C_2$-$C_6$ alkenyl group, i.e., a branched or linear alkenyl group having from 2 to about 6 carbons. In still other preferred embodiments, the alkenyl group is a $C_3$-$C_{10}$ alkenyl group, i.e., a branched or linear alkenyl group having from about 3 to about 10 carbons. In yet other preferred embodiments, the alkenyl group is a $C_2$-$C_5$ alkenyl group, i.e., a branched or linear alkenyl group having from 2 to about 5 carbons. Exemplary alkenyl groups include, for example, vinyl, propenyl, butenyl, pentenyl hexenyl, heptenyl, octenyl, nonenyl and decenyl groups.

As used herein, "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, "aralkyl" refers to alkyl radicals bearing an aryl substituent and have from about 6 to about 50 carbon atoms (and all combinations and subcombinations of ranges and specific numbers of carbon atoms therein), with from about 6 to about 10 carbon atoms being preferred. Aralkyl groups can be optionally substituted in either the aryl or alkyl portions. Non-limiting examples include, for example, phenylmethyl (benzyl), diphenylmethyl, triphenylmethyl, phenylethyl, diphenylethyl and 3-(4-methylphenyl)propyl.

As used herein, "heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

As used herein, "cycloalkyl" refers to an optionally substituted, alkyl group having one or more rings in their structures having from about 3 to about 20 carbon atoms (and all combinations and subcombinations of ranges and specific numbers of carbon atoms therein), with from about 3 to about 10 carbon atoms being preferred, with from about 3 to about 8 carbon atoms being more preferred, with from about 3 to about 6 carbon atoms being even more preferred. Multi-ring structures may be bridged or fused ring structures. The cycloalkyl group may be optionally substituted with, for example, alkyl, preferably $C_1$-$C_3$ alkyl, alkoxy, preferably $C_1$-$C_3$ alkoxy, or halo. Non-limiting examples include, for example, cyclopropyl, cyclobutyl, cyclopentyl, cyclohexyl, cycloheptyl cyclooctyl, and adamantyl.

As used herein, "cycloalkyl-substituted alkyl" refers to a linear alkyl group, preferably a lower alkyl group, substituted at a terminal carbon with a cycloalkyl group, preferably a $C_3$-$C_8$ cycloalkyl group. Non-limiting examples include, for example, cyclohexylmethyl, cyclohexylethyl, cyclopentylethyl, cyclopentylpropyl, cyclopropylmethyl, and the like.

As used herein, "cycloalkenyl" refers to an olefinically unsaturated cycloalkyl group having from about 4 to about 10 carbons, and all combinations and subcombinations of ranges therein. In preferred embodiments, the cycloalkenyl group is a $C_5$-$C_8$ cycloalkenyl group, i.e., a cycloalkenyl group having from about 5 to about 8 carbons.

As used herein, "alkylcycloalkyl" refers to an optionally substituted ring system comprising a cycloalkyl group having one or more alkyl substituents. Non-limiting examples include, for example, alkylcycloalkyl groups include 2-methylcyclohexyl, 3,3-dimethylcyclopentyl, trans-2,3-dimethylcyclooctyl, and 4-methyldecahydronaphthalenyl.

As used herein, "heteroaralkyl" refers to an optionally substituted, heteroaryl substituted alkyl radicals having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, "heterocycloalkyl" refers to an optionally substituted, mono-, di-, tri-, or other multicyclic aliphatic ring system that includes at least one, and preferably from 1 to about 4 sulfur, oxygen, or nitrogen heteroatom ring members. Heterocycloalkyl groups can have from about 3 to about 20 carbon atoms (and all combinations and subcombinations of ranges and specific numbers of carbon atoms therein), with from about 4 to about 10 carbons being preferred. The heterocycloalkyl group may be unsaturated, and may also be fused to aromatic rings. Non-limiting examples include, for example, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperadinyl, decahydroquinolyl, octahydrochromenyl, octahydrocyclopenta[c]pyranyl, 1,2,3,4,-tetrahydroquinolyl, octahydro-[2]pyrindinyl, decahydro-cycloocta[c]furanyl, and imidazolidinyl.

As used herein, the term "spiroalkyl" refers to an optionally substituted, alkylene diradical, both ends of which are bonded to the same carbon atom of the parent group to form a spirocyclic group. The spiroalkyl group, taken together with its parent group, as herein defined, has 3 to 20 ring atoms. Preferably, it has 3 to 10 ring atoms. Non-limiting examples of a spiroalkyl group taken together with its parent group include 1-(1-methyl-cyclopropyl)-propan-2-one, 2-(1-phenoxy-cyclopropyl)-ethylamine, and 1-methyl-spiro[4.7]dodecane.

As used herein, the term "alkoxy" refers to an optionally substituted alkyl-O— group wherein alkyl is as previously defined. Non-limiting examples include, for example, include methoxy, ethoxy, n-propoxy, i-propoxy, n-butoxy, and heptoxy.

As used herein, the term "aryloxy" refers to an optionally substituted aryl-O— group wherein aryl is as previously defined. Non-limiting examples include, for example, phenoxy and naphthoxy.

As used herein, the term "aralkoxy" refers to an optionally substituted aralkyl-O— group wherein aralkyl is as previously defined. Non-limiting examples include, for example, benzyloxy, 1-phenylethoxy, 2-phenylethoxy, and 3-naphthylheptoxy.

As used herein, the term "aryloxyaryl" refers to an aryl group with an aryloxy substituent wherein aryloxy and aryl are as previously defined. Aryloxyaryl groups can be optionally substituted. Non-limiting examples include, for example, phenoxyphenyl, and naphthoxyphenyl.

As used herein, the term "heteroarylaryl" refers to an aryl group with a heteroaryl substituent wherein heteroaryl and aryl are as previously defined. Heteroarylaryl groups can be optionally substituted. Non-limiting examples include, for example, 3-pyridylphenyl, 2-quinolylnaphthalenyl, and 2-pyrrolylphenyl.

As used herein, the term "alkoxyaryl" refers to an aryl group bearing an alkoxy substituent wherein alkoxy and aryl are as previously defined. Alkoxyaryl groups can be optionally substituted. Non-limiting examples include, for example, para-anisyl, meta-t-butoxyphenyl, and methylendioxyphenyl.

As used herein, "carboxy" refers to a —C(=O)OH group.

As used herein, "alkanoyl" refers to a —C(=O)-alkyl group, wherein alkyl is as previously defined. Exemplary alkanoyl groups include acetyl (ethanoyl), n-propanoyl, n-butanoyl, 2-methylpropanoyl, n-pentanoyl, 2-methylbutanoyl, 3-methylbutanoyl, 2,2-dimethylpropanoyl, heptanoyl, decanoyl, and palmitoyl.

As used herein, "heterocyclic" refers to a monocyclic or multicyclic ring system carbocyclic radical containing from about 4 to about 10 members, and all combinations and subcombinations of ranges therein, wherein one or more of the members is an element other than carbon, for example, nitrogen, oxygen or sulfur. The heterocyclic group may be aromatic or nonaromatic. Non-limiting examples include, for example, pyrrole and piperidine groups.

As used herein, "halo" refers to fluoro, chloro, or bromo.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), nitro (—NO$_2$), cyano (—CN), amino (—NH$_2$), —N-substituted amino (—NHR"), —N,N-disubstituted amino (—N(R")R"), carboxyl (—COOH), —C(=O)R", —OR", —C(=O)OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (SR"), sulfonic acid (SO$_3$H), phosphonic acid (PO$_3$H), S(=O)$_2$R", S(=O)$_2$NH$_2$, S(=O)$_2$NHR", S(=O)$_2$NR"R", NHS(=O)$_2$R", NR"S(=O)$_2$R", CF$_3$, CF$_2$CF$_3$, NHC(=O)NHR", NHC(=O)NR"R", NR"C(=O)NHR", NR"C(=O)NR"R", NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example.

As used herein, "side effect" refers to a consequence other than the one(s) for which an agent or measure is used, as the adverse effects produced by a drug, especially on a tissue or organ system other then the one sought to be benefited by its administration. In the case, for example, of opioids, the term "side effect" may refer to such conditions as, for example, ileus, pruritis, constipation, urinary retention, biliary spasm, opioid bowel dysfunction, colic, nausea, or vomiting or a combination thereof.

As used herein, "ileus" refers to the obstruction of the bowel or gut, especially the colon. See, e.g., *Dorland's Illustrated Medical Dictionary*, p. 816, 27th ed. (W.B. Saunders Company, Philadelphia 1988). Ileus should be distinguished from constipation, which refers to infrequent or difficulty in evacuating the feces. See, e.g., *Dorland's Illustrated Medical Dictionary*, p. 375, 27th ed. (W.B. Saunders Company, Philadelphia 1988). Ileus may be diagnosed by the disruption of normal coordinated movements of the gut, resulting in failure of the propulsion of intestinal contents. See, e.g., Resnick, *J. Am. J. of Gastroenterology*, 1992, 751 and Resnick, *J. Am. J. of Gastroenterology*, 1997, 92, 934. In some instances, particularly following surgery, including surgery of the abdomen, the bowel dysfunction may become quite severe, lasting for more than a week and affecting more than one portion of the gastrointestinal tract. This condition is often referred to as postsurgical (or postoperative) ileus and most frequently occurs after laparotomy (see Livingston, E. H. and Passaro, E. D. Jr., *Digestive Diseases and Sciences*, 1990, 35, 121). Similarly, postpartum ileus is a common problem for women in the period following childbirth, and is thought to be caused by similar fluctuations in natural opioid levels as a result of birthing stress.

As used herein, "effective amount" refers to an amount of a compound as described herein that may be therapeutically effective to inhibit, prevent, or treat the symptoms of particular disease, disorder, or side effect. Such diseases, disorders and side effects include, but are not limited to, those pathological conditions associated with the administration of opioids (for example, in connection with the treatment and/or prevention of pain), wherein the treatment or prevention comprises, for example, inhibiting the activity thereof by contacting cells, tissues or receptors with compounds of the present invention. Thus, for example, the term "effective amount," when used in connection with opioids, for example, for the treatment of pain, refers to the treatment and/or prevention of the painful condition. The term "effective amount," when used in connection with peripheral µ opioid antagonists, refers to the treatment and/or prevention of side effects typically associated with opioids including, for example, such side effects as ileus, pruritis, constipation, urinary retention, biliary spasm, opioid bowel dysfunction, colic, nausea, or vomiting or a combination thereof.

As used herein, "in combination with," "combination therapy" and "combination products" refer, in certain embodiments, to the concurrent administration to a patient of antiemetic agents and peripheral µ opioid antagonists, including, for example, the compounds of formula I, or to the concurrent administration to a patient of antiemetic agents, peripheral µ opioid antagonists, and opioids. When administered in combination, each component may be administered at the same time or sequentially in any order at different points in time. Thus, each component may be administered separately but sufficiently closely in time so as to provide the desired therapeutic effect.

As used herein, "dosage unit" refers to physically discrete units suited as unitary dosages for the particular patient to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable metal salt" refer to derivatives of the disclosed compounds wherein the parent compound is modified by making base salts thereof. Examples of pharmaceutically acceptable salts include, but are not limited to, mineral or organic acid salts of basic residues such as amines, alkali and the like. The pharmaceutically acceptable salts include the conventional non-toxic salts of the parent compound formed, for example, from non-toxic inorganic or organic bases. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. Isomorphic crystalline forms, all chiral and racemic forms, N-oxide, hydrates, and solvates are also contemplated to be within the scope of the present invention.

Certain acidic or basic compounds of the present invention may exist as zwitterions. All forms of the compounds, including free acid, free-base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

As used herein, "patient" refers to animals, including mammals, preferably humans.

As used herein, "prodrug" refers to compounds specifically designed to maximize the amount of active species that reaches the desired site of reaction that are of themselves typically inactive or minimally active for the activity desired, but through biotransformation are converted into biologically active metabolites.

As used herein, "stereoisomers" refers to compounds that have identical chemical constitution, but differ as regards the arrangement of the atoms or groups in space.

As used herein, "N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

The piperidines derivatives useful in the methods, compositions, and kits of the invention as illustrated in formula I can occur as the trans and cis stereochemical isomers at the 3- and 4-positions of the piperidine ring. In the most preferred compounds of formula I, the $R^2$ substituent and the $R^4$ substituent are in the "trans" orientation on the piperidine.

In addition to the "cis" and "trans" orientation of the $R^2$ substituent and the $R^4$ substituent of formula I, the absolute stereochemistry of the carbon atoms bearing $R^2$ substituent and the $R^4$ substituent of formula I is also defined as using the commonly employed "R" and "S" definitions (Orchin et al., *The Vocabulary of Organic Chemistry*, John Wiley and Sons, Inc., page 126, which is incorporated herein by reference). The preferred compounds of the present invention are those in which the configuration of both the $R^2$ substituent and the $R^4$ substituents of formula I on the piperidine ring are "R."

Furthermore, asymmetric carbon atoms may be introduced into the molecule depending on the structure of $R^4$. As such, these classes of compounds can exist as the individual "R" or "S" stereoisomers at these chiral centers, or the racemic mixture of the isomers, and all are contemplated as within the scope of the present invention. Preferably, a substantially pure stereoisomer of the compounds of this invention is used, i.e., an isomer in which the configuration at the chiral center is "R" or "S", i.e., those compounds in which the configuration at the three chiral centers I preferably 3R, 4R, S or 3R, 4R, R.

As used herein, "peripheral" or "peripherally-acting" refers to an agent that acts outside of the central nervous system.

As used herein, "centrally-acting" refers to an agent that acts within the central nervous system.

The methods, compositions, and kits of the present invention involve a peripheral opioid antagonist compound. The term "peripheral" designates that the compound acts primarily on physiological systems and components external to the central nervous system. In preferred form, the peripheral opioid antagonist compounds employed in the methods of the present invention exhibit high levels of activity with respect to peripheral tissue, such as, gastrointestinal tissue, while exhibiting reduced, and preferably substantially no, CNS activity. The phrase "substantially no CNS activity," as used herein, means that less than about 20% of the pharmacological activity of the compounds employed in the present methods is exhibited in the CNS, preferably less than about 15%, more preferably less than about 10%, even more preferably less than about 5% and most preferably less than about 1% of the pharmacological activity of the compounds employed in the present methods is exhibited in the CNS.

Furthermore, it is preferred in certain embodiments of the invention where the compound is administered to antagonize the peripheral side effects of an opioid that the compound does not substantially cross the blood-brain barrier and thereby decrease the beneficial activity of the opioid. The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and most preferably 0% by weight of the compound crosses the blood-brain barrier. Selected compounds can be evaluated for CNS penetration by determining plasma and brain levels following intravenous administration.

U.S. Pat. No. 6,451,806 and U.S. Pat. No. 6,469,030 disclose methods and compositions comprising opioids and opioid antagonists, including peripheral μ opioid antagonists, the disclosures of which are incorporated herein by reference in their entirety. The methods and compositions are useful, inter alia, for treating and/or preventing pain and for treating and/or preventing side effects associated with opioids including ileus, pruritis, constipation, urinary retention, biliary spasm, opioid bowel dysfunction, colic, vomiting or nausea or a combination thereof, particularly postoperative or postpartum ileus, opioid bowel dysfunction, postoperative nausea, or postoperative vomiting. The methods, compositions, and kits of the present invention are related to peripheral μ opioid antagonists and are directed to combinations of peripheral μ opioid antagonists with centrally-acting antiemetic agents and with centrally-acting antiemetic agents and opioids, for the treatment and prevention, for example, of pain and/or side effects associated with opioids, including ileus, pruritis, constipation, urinary retention, biliary spasm, opioid bowel dysfunction, colic, vomiting or nausea or a combination thereof, particularly postoperative or postpartum ileus, opioid bowel dysfunction, postoperative nausea, or postoperative vomiting.

Accordingly, in one embodiment, the present invention provides methods comprising the steps of:
a. providing a composition, comprising:
   (i) a pharmaceutically-acceptable metal salt of at least one compound of formula I:

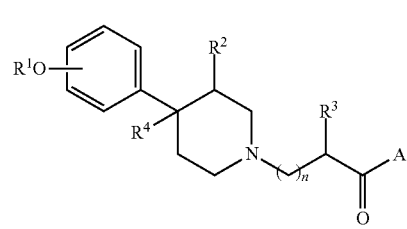

wherein:
$R^1$ is hydrogen or alkyl;
$R^2$ is hydrogen, alkyl or alkenyl;
$R^3$ is hydrogen, alkyl, alkenyl, aryl, cycloalkyl, cycloalkenyl, cycloalkyl-substituted alkyl, cycloalkenyl-substituted alkyl or aralkyl;
$R^4$ is hydrogen, alkyl or alkenyl;
A is $OR^5$ or $NR^6R^7$;
$R^5$ is hydrogen, alkyl, alkenyl, cycloalkyl, cycloalkenyl, cycloalkyl-substituted alkyl, cycloalkenyl-substituted alkyl, or aralkyl;
$R^6$ is hydrogen or alkyl;
$R^7$ is hydrogen, alkyl, alkenyl, cycloalkyl, aryl, cycloalkyl-substituted alkyl, cycloalkenyl, cycloalkenyl-substituted alkyl, aralkyl, aralkyl, or alkylene substituted B or, together with the nitrogen atom to which they are attached, $R^6$ and $R^7$ form a heterocyclic ring;

B is

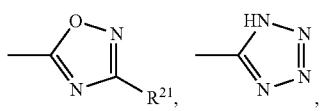

C(=O)W or $NR^8R^9$;

$R^8$ is hydrogen or alkyl;

$R^9$ is hydrogen, alkyl, alkenyl, cycloalkyl-substituted alkyl, cycloalkyl, cycloalkenyl, cycloalkenyl-substituted alkyl, aryl or aralkyl or, together with the nitrogen atom to which they are attached, $R^8$ and $R^9$ form a heterocyclic ring;

W is $OR^{10}$, $NR^{11}R^{12}$, or OE;

$R^{10}$ is hydrogen, alkyl, alkenyl, cycloalkyl, cycloalkenyl, cycloalkyl-substituted alkyl, cycloalkenyl-substituted alkyl, or aralkyl;

$R^{11}$ is hydrogen or alkyl;

$R^{12}$ is hydrogen, alkyl, alkenyl, aryl, cycloalkyl, cycloalkenyl, cycloalkyl-substituted alkyl, cycloalkenyl-substituted alkyl, aralkyl or alkylene substituted C(=O)Y or, together with the nitrogen atom to which they are attached, $R^{11}$ and $R^{12}$ form a heterocyclic ring;

E is

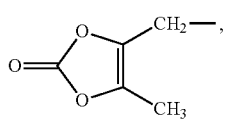

alkylene substituted (C=O)D, or —$R^{13}OC(=O)R^{14}$;

$R^{13}$ is alkyl substituted alkylene;

$R^{14}$ is alkyl;

D is $OR^{15}$ or $NR^{16}R^{17}$;

$R^{15}$ is hydrogen, alkyl, alkenyl, cycloalkyl, cycloalkenyl, cycloalkyl-substituted alkyl, cycloalkenyl-substituted alkyl, or aralkyl;

$R^{16}$ is hydrogen, alkyl, alkenyl, aryl, aralkyl, cycloalkyl, cycloalkenyl, cycloalkyl-substituted alkyl or cycloalkenyl-substituted alkyl;

$R^{17}$ is hydrogen or alkyl or, together with the nitrogen atom to which they are attached, $R^{16}$ and $R^{17}$ form a heterocyclic ring;

Y is $OR^{18}$ or $NR^{19}R^{20}$;

$R^{18}$ is hydrogen, alkyl, alkenyl, cycloalkyl, cycloalkenyl, cycloalkyl-substituted alkyl, cycloalkenyl-substituted alkyl, or aralkyl;

$R^{19}$ is hydrogen or alkyl;

$R^{20}$ is hydrogen, alkyl, alkenyl, aryl, cycloalkyl, cycloalkenyl, cycloalkyl-substituted alkyl, cycloalkenyl-substituted alkyl, or aralkyl or, together with the nitrogen atom to which they are attached, $R^{19}$ and $R^{20}$ form a heterocyclic ring;

$R^{21}$ is hydrogen or alkyl; and n is 0 to 4;

(ii) at least one bulking agent that crystallizes;
(iii) at least one weak base; and
(iv) water;
wherein said composition has an initial pH of at least about 10.5; and b. adjusting the pH of said composition to a final pH in the range of about 9 to about 11;

wherein, upon administration to a patient, said composition has improved solubility and bioavailability for oral or parenteral administration.

The methods of the present invention are useful, inter alia, for forming composition having improved solubility and bioavailability, particularly via injectable formulations, such as those administered intravenously, relative to prior art compositions, including compositions containing the same or different components that have not been processed in the same way to form the final formulation (such as pH adjustments, forming the pharmaceutically-acceptable metal salt of the active ingredient in situ, lyophilization, and/or annealing) or that do not have same physical properties (such as density or porosity).

In preferred embodiments of the method, upon reconstitution the solution is formed in less than about five minutes under ambient conditions, more preferably, less than about one minute under ambient conditions, and, even more preferably, less than about 30 seconds under ambient conditions, preferably by simple shaking, stirring, or mixing. As used herein, "under ambient conditions" means under normal atmospheric pressure and room temperature in the range of about 10° C. to about 50° C. without the addition of direct heating or cooling. The formation of the solution may determined, for example, by the presence of a clear solution upon mixing by visual observation, preferably using a microscope light projected through a diaphragm into the solution, by Coulter counter, or by light-scattering instruments.

In preferred embodiments of the method, the initial pH is adjusted to at least about 11. Preferably, the initial pH does not exceed about pH 12, as this high pH may lead to instability of the composition. The initial pH may be adjusted with any suitable pharmaceutically acceptable pH adjusting agent, including a strong or weak acid or base, preferably pharmaceutically-acceptable metal carbonate, pharmaceutically-acceptable metal bicarbonate, pharmaceutically-acceptable metal hydroxide, or hydrochloric acid, more preferably where the pharmaceutically-acceptable metal is sodium, and even more preferably, sodium carbonate or sodium bicarbonate, and yet more preferably sodium carbonate. Sodium carbonate and sodium bicarbonate are preferred because they generate carbon dioxide and thereby contribute to the desirable lower density of the composition.

In preferred embodiments of the method, the final pH is adjusted to a range of about 9.5 to about 10.5. The final pH may be adjusted with any suitable pharmaceutically acceptable pH adjusting agent, including a strong or weak acid or base, preferably sodium hydroxide or hydrochloric acid.

In certain preferred embodiments of the method, the pharmaceutically-acceptable metal salt of at least one compound of formula I is prepared in situ.

In certain preferred embodiments of the method, the pharmaceutically-acceptable metal salt of the compound of formula I is formed from at least one weak base, wherein said weak base is added in at least about an equimolar amount to the compound of formula I. Preferably, there is not a great excess of weak base, as such excess may lead to an undesirably high pH (greater than about 12) which may contribute to instability of the composition.

In certain preferred embodiments of the method, the composition is prepared by first admixing said bulking agent and a pharmaceutically-acceptable metal salt of said weak base in water and then adding said compound of formula I to said admixture.

In certain other preferred embodiments of the method, the composition is prepared by substantially simultaneously admixing said compound of formula I, said bulking agent and a pharmaceutically-acceptable metal salt of said weak base in water. As used in the context of admixing, "substantially simultaneously" refers to adding the components together within about five minutes, preferably within about one minute, and more preferably within about 30 seconds of each other.

In preferred embodiments of the invention, the pharmaceutically acceptable metal is an alkali metal, such as sodium, potassium, or lithium, or an alkaline earth metal, such as calcium, or magnesium, or combinations thereof. Sodium, calcium, and magnesium are preferred. Sodium is more preferred. It is preferred to avoid potassium for parenteral administration.

The method may further comprise the step of drying said composition to remove at least a portion of said water to form a partially or fully dried product. In preferred embodiments, the composition is annealed during the drying step. As used herein, "annealed" means the process of heating and then slowly cooling a material, including repeated cycles of heating and cooling. Suitable drying means include lyophilization (freeze-drying), spray drying, vacuum drying, and combinations thereof. The preferred drying means is via lyophilization.

The method may yet further comprise the step of reconstituting said dried product by combining therewith a pharmaceutically acceptable solvent to form a solution of said dried product.

In preferred embodiments of the method, the weak base is bicarbonate or carbonate, more preferably carbonate. These weak bases are preferred because they generate carbon dioxide and thereby contribute to the desirable lower density of the composition.

In preferred embodiments of the method, the pharmaceutically acceptable solvent is aqueous, preferably, water, isotonic sodium chloride solution, Ringer's solution, dextrose solution, or lactated Ringer's solution.

In preferred embodiments, the method of the invention further comprises the step of administering said solution of said dried product to a patient. The composition may be administered prior to surgery, during surgery, and/or in the absence of surgery.

In preferred embodiments, the composition is administered via injection, particularly subcutaneous injection, intramuscular injection, or intravenous injection.

Any pharmaceutically acceptable bulking agent that crystallizes may be used in the composition of the invention. As used herein, "bulking agent" refers to an inert diluent or filler that acts as a carrying agent for the drug substance (in the case of the present invention, the compound of formula I). Suitable bulking agents may be found in the *Handbook of Pharmaceutical Excipients*, 3$^{rd}$ Ed. Washington, D.C: American Pharmaceutical Association, 1998, the disclosure of which is incorporated herein by reference. In certain other preferred embodiments, the bulking agent is a polyol, such as a carbohydrate or sugar alcohol. Suitable carbohydrates include sucrose, trehalose, lactose, maltose, and mixtures thereof. Suitable sugar alcohols include mannitol, xylitol, erythritol, lactitol, isomalt, polyalditol, maltitol, and mixtures thereof. Mannitol is particularly preferred.

While not wishing to be bound by theory, it is believed that bulking agents that crystallize produce a desirable cake structure with good mechanical properties. These properties are important to ensure rapid reconstitution rates. Additionally, rapid nucleation of a bulking agent that crystallizes during lyophilization produces a cake with a much greater surface area, thus resulting in higher diffusive flux and faster sublimation rates. Bulking agents that are in an amorphous form require a high amount of energy to dry and do not produce a desirable cake structure. Since initial ice crystal size depends upon contributions from nucleation and growth rate, small ice crystals formed in systems containing amorphous solids produce pores with lower surface area per volume. This lower surface area results in lower diffusive flux and lower sublimation rates.

In certain embodiments, the invention is directed to compositions, comprising:
a. a pharmaceutically-acceptable metal salt of at least one compound of formula I;
b. at least one bulking agent that crystallizes;
wherein said composition has a density of less than about 1.0 g/cm$^3$;
wherein, upon administration to a patient, said composition has improved solubility and bioavailability for oral or parenteral administration.
Preferably, the composition has a density of less than about 0.5 g/cm$^3$, more preferably, less than about 0.2 g/cm$^3$, even more preferably less than about 0.15 g/cm$^3$, yet even more preferably in the range of about 0.05 g/cm$^3$ to about 0.12 g/cm$^3$, more preferably, a density in the range of about 0.06 g/cm$^3$ to about 0.08 g/cm$^3$.

In certain other embodiments, the invention is directed to compositions, comprising:
a. a pharmaceutically-acceptable metal salt of at least one compound of formula I;
b. at least one bulking agent that crystallizes;
c. less than about 0.5% by weight, based on the total weight of the composition, of a solubilizing surfactant;
d. less than about 10% by weight, based on the total weight of the composition, of a non-aqueous solvent; and
e. less than about 0.5% by weight, based on the total weight of the composition, of cyclodextrin;
wherein, upon administration to a patient, said composition has improved solubility and bioavailability for oral or parenteral administration.

These compositions provide improved solubility and bioavailability for oral or parenteral administration because they permit the compound of formula I to more readily go into solution when reconstituted from dried product than would otherwise be the case for the compounds of formula I, which have a very low water solubility due to their zwitterionic nature.

Preferably, the pharmaceutically-acceptable metal salt of a compound of formula I is present at a level of at least about 0.1 mg/mL, more preferably, at a level of at least about 1 mg/mL, and even more preferably, at a level of at least about 2 mg/mL.

Preferably, compositions of the invention further comprising at least one pharmaceutically acceptable solvent. In preferred embodiments of the composition, the pharmaceutically acceptable solvent is aqueous, preferably, water, isotonic sodium chloride solution, Ringer's solution, dextrose solution, or lactated Ringer's solution.

Preferably, the composition has a shelf life of at least about 18 months. As used herein, "shelf life" refers to the time from the date of manufacture and packing of the formulation, until its chemical or biological activity is not less than a predetermined level of labeled potency, generally about 90%, and its physical characteristics have not changed appreciably or deleteriously.

In certain preferred embodiments, the compositions of the invention may include an opioid, a prodrug of an opioid, and/or pharmacologically-active metabolites, provided that its inclusion does not interfere with the solubility or bioavailability of the compound of formula I. Suitable opioids include alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol, and mixtures thereof. Preferred opioids include morphine, codeine, oxycodone, hydrocodone, dihydrocodeine, propoxyphene, fentanyl, and tramadol.

Compositions of the present invention may further include one or more other active ingredients conventionally employed in analgesic and/or cough-cold-antitussive combination products, provided that its inclusion does not interfere with the solubility or bioavailability of the compound of formula I. Such conventional ingredients include, for example, aspirin, COX-2 inhibitors, acetaminophen, phenylpropanolamine, phenylephrine, chlorpheniramine, caffeine, and/or guaifenesin. Typical or conventional ingredients that may be included are described, for example, in the *Physicians' Desk Reference,* 2004, the disclosure of which is hereby incorporated herein by reference, in its entirety.

In addition, the composition of the invention may further include one or more compounds that may be designed to enhance the analgesic potency of the opioid and/or to reduce analgesic tolerance development, provided that its inclusion does not interfere with the solubility or bioavailability of the compound of formula I. Such compounds include, for example, dextromethorphan or other NMDA antagonists (Mao, M. J. et al., *Pain* 1996, 67, 361), L-364,718 and other CCK antagonists (Dourish, C. T. et al., *Eur. J. Pharmacol.,* 1988, 147, 469), NOS inhibitors (Bhargava, H. N. et al., *Neuropeptides,* 1996, 30, 219), PKC inhibitors (Bilsky, E. J. et al., *J. Pharmacol. Exp. Ther.* 1996, 277, 484), and dynorphin antagonists or antisera (Nichols, M. L. et al., *Pain,* 1997, 69, 317). The disclosures of each of the foregoing documents are hereby incorporated herein by reference, in their entireties.

Other opioids, optional conventional opioid components, and optional compounds for enhancing the analgesic potency of the opioid and/or for reducing analgesic tolerance development, that may be employed in the methods and compositions of the present invention, in addition to those exemplified above, would be readily apparent to one of ordinary skill in the art, once armed with the teachings of the present disclosure.

Preferred 4-aryl-piperidine derivatives include, for example, the compounds disclosed in U.S. Pat. No. 5,250,542; U.S. Pat. No. 5,159,081; U.S. Pat. No. 5,270,328; and U.S. Pat. No. 5,434,171, U.S. Pat. No. 6,451,806 and U.S. Pat. No. 6,469,030, the disclosures of which are hereby incorporated herein by reference, in their entireties.

In preferred embodiments, the compound of formula I is a trans 3,4-isomer.

In certain embodiments employing compounds of formula I, it is preferred that
$R^1$ is hydrogen;
$R^2$ is alkyl;
n is 1 or 2;
$R^3$ is benzyl, phenyl, cyclohexyl, or cyclohexylmethyl; and
$R^4$ is alkyl.

In certain embodiments employing compounds of formula I, it is preferred that
A is $OR^5$; and
$R^5$ is hydrogen or alkyl.

In certain embodiments employing compounds of formula I, it is preferred that
A is $NR^6R^7$;
$R^6$ is hydrogen;
$R^7$ is alkylene substituted B; and
B is C(O)W.

In certain embodiments employing compounds of formula I, it is preferred that
$R^7$ is $(CH_2)_q$—B;
q is about 1 to about 3;
W is $OR^{10}$; and
$R^{10}$ is hydrogen, alkyl, phenyl-substituted alkyl, cycloalkyl or cycloalkyl-substituted alkyl.

In certain embodiments including compounds of formula I, it is preferred that
W is $NR^{11}R^{12}$
$R^{11}$ is hydrogen or alkyl; and
$R^{12}$ is hydrogen, alkyl or alkylene substituted C(=O)Y.

In certain embodiments employing compounds of formula I, it is preferred that
$R^{12}$ is $(CH_2)_mC(O)Y$;
m is 1 to 3;
Y is $OR^{18}$ or $NR^{19}R^{20}$; and
$R^{18}$, $R^{19}$ and $R^{20}$ are independently hydrogen or alkyl.

In certain embodiments employing compounds of formula I, it is preferred that
W is OE;
E is $CH_2C(=O)D$;
D is $OR^{15}$ or $NR^{16}R^{17}$;
$R^{15}$ is hydrogen or alkyl;
$R^{16}$ is methyl or benzyl; and
$R^{17}$ is hydrogen.

In certain embodiments employing compounds of formula I, it is preferred that
W is OE;
E is $R^{13}OC(=O)R^{14}$;
$R^{13}$ is —CH(CH$_3$)— or —CH(CH$_2$CH$_3$)—; and
$R^{14}$ is alkyl.

In certain embodiments employing compounds of formula I, it is preferred that
A is $OR^S$; and
$R^5$ is hydrogen.

In certain embodiments employing compounds of formula I, it is preferred that the configuration at positions 3 and 4 of the piperidine ring is each R.

Preferred compounds of formula I include:
Q-CH$_2$CH(CH$_2$(C$_6$H$_5$))C(O)OH,
Q-CH$_2$CH$_2$CH(C$_6$H$_5$)C(O)NHCH$_2$C(O)OCH$_2$CH$_3$,
Q-CH$_2$CH$_2$CH(C$_6$H$_5$)C(O)NHCH$_2$C(O)OH,
Q-CH$_2$CH$_2$CH(C$_6$H$_5$)C(O)NHCH$_2$C(O)NHCH$_3$,
Q-CH$_2$CH$_2$CH(C$_6$H$_5$)C(O)NHCH$_2$C(O)NHCH$_2$CH$_3$,
G-NH(CH$_2$)$_2$C(O)NH$_2$,
G-NH(CH$_2$)$_2$C(O)NHCH$_3$,
G-NHCH$_2$C(O)NH$_2$,
G-NHCH$_2$C(O)NHCH$_3$,
G-NHCH$_2$C(O)NHCH$_2$CH$_3$,
G-NH(CH$_2$)$_3$C(O)OCH$_2$CH$_3$,
G-NH(CH$_2$)$_3$C(O)NHCH$_3$,
G-NH(CH$_2$)$_2$C(O)OH,
G-NH(CH$_2$)$_3$C(O)OH,
Q-CH$_2$CH(CH$_2$(C$_6$H$_{11}$))C(O)NHCH$_2$C(O)OH,
Q-CH$_2$CH(CH$_2$(C$_6$H$_{11}$))C(O)NH(CH$_2$)$_2$C(O)OH,
Q-CH$_2$CH(CH$_2$(C$_6$H$_{11}$))C(O)NH(CH$_2$)$_2$C(O)NH$_2$, Z—NHCH$_2$C(O)OCH$_2$CH$_3$,
Z—NHCH$_2$C(O)OH,
Z—NHCH$_2$C(O)NH$_2$,
Z—NHCH$_2$C(O)N(CH$_3$)$_2$,
Z—NHCH$_2$C(O)NHCH(CH$_3$)$_2$,
Z—NHCH$_2$C(O)OCH$_2$CH(CH$_3$)$_2$,
Z—NH(CH$_2$)$_2$C(O)OCH$_2$(C$_6$H$_5$),
Z—NH(CH$_2$)$_2$C(O)OH,
Z—NH(CH$_2$)$_2$C(O)NHCH$_2$CH$_3$,
Z—NH(CH$_2$)$_3$C(O)NHCH$_3$,
Z—NHCH$_2$C(O)NHCH$_2$C(O)OH,
Z—NHCH$_2$C(O)OCH$_2$C(O)OCH$_3$,
Z—NHCH$_2$C(O)O(CH$_2$)$_4$CH$_3$,
Z—NHCH$_2$C(O)OCH$_2$C(O)NHCH$_3$,
Z—NHCH$_2$C(O)O-(4-methoxycyclohexyl),
Z—NHCH$_2$C(O)OCH$_2$C(O)NHCH$_2$(C$_6$H$_5$) and
Z—NHCH$_2$C(O)OCH(CH$_3$)OC(O)CH$_3$;
wherein:
Q represents

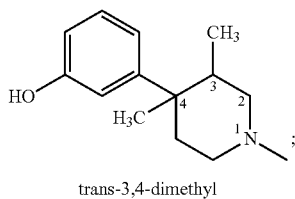 [SMILES: CC1CN(C)CCC1(C)c1cccc(O)c1 ; ";"]

trans-3,4-dimethyl

G represents

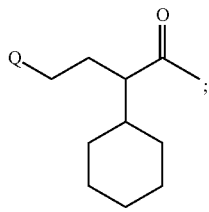

and
Z represents

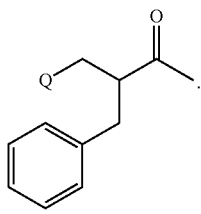

More preferred compounds of formula I include:
(3R,4R,S)—Z—NHCH$_2$C(O)OCH$_2$CH(CH$_3$)$_2$,
(+)-Z—NHCH$_2$C(O)OH,
(−)-Z—NHCH$_2$C(O)OH,
(3R,4R,R)—Z—NHCH$_2$C(O)—OCH$_2$CH(CH$_3$)$_2$,
(3S,4S,S)—Z—NHCH$_2$C(O)OCH$_2$CH(CH$_3$)$_2$,
(3S,4S,R)—Z—NHCH$_2$C(O)OCH$_2$CH(CH$_3$)$_2$,
(3R,4R)—Z—NHCH$_2$C(O)NHCH$_2$(C$_6$H$_5$) and
(3R,4R)-G-NH(CH$_2$)$_3$C(O)OH.
wherein Q, Z and G are as defined above.
Even more preferred compounds of formula I include (+)-Z—NHCH$_2$C(O)OH and (−)-Z—NHCH$_2$C(O)OH, wherein Z is as defined above. It is especially preferred when said compound is (+)-Z—NHCH$_2$C(O)OH. [[2(S)[[4(R)-(3-hydroxyphenyl)-3(R),4-dimethyl-piperidinyl]methyl]-1-oxo-3-phenylpropyl]amino]acetic acid dihydrate (USAN name alvimopan) is an especially preferred compound.

Even more preferred compounds of formula I include Q-CH$_2$CH(CH$_2$(C$_6$H$_5$))C(O)OH, wherein Q is as defined above. It is especially preferred when said compound is (3R, 4R, S)-Q-CH$_2$CH(CH$_2$(C$_6$H$_5$))C(O)OH. This compound is an active metabolite of alvimopan but, when administered orally, has a much greater propensity for undesirably reversing analgesia than alvimopan. When administered parenterally, especially intraveneously, it may be administered at much lower doses with an attendant reduction in this propensity.

Compounds of formula I that act locally on the gut, have high potency, and are orally active are particularly preferred. A particularly preferred embodiment of the present invention is the compound (+)-Z—NHCH$_2$C(O)OH, i.e., the compound of the following formula (II):

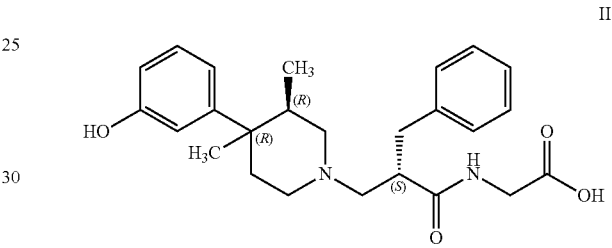

II

The compound of formula (II) has low solubility in water except at low or high pH conditions. Zwitterionic character may be inherent to the compound, and may impart desirable properties such as poor systemic absorption and sustained local effect on the gut following oral administration.

In especially preferred embodiments, the compound of a formula I is a substantially pure stereoisomer.

In yet another embodiment, the invention is directed to injectable dosage formulations, comprising the above-described compositions. In preferred embodiments, the injectable dosage formulations contribute minimal or no additional pain on injection relative to the pain caused by venipuncture, despite the fact that the composition containing the active ingredient was prepared at a pH higher than physiological pH.

In yet other embodiments, the invention is directed to methods of preventing or treating a side effect associated with an opioid in a patient, comprising the step of:
administering to said patient in need thereof an effective amount of the above-described composition.

The methods are useful in the prevention and treatment of ileus, pruritis, constipation, urinary retention, biliary spasm, opioid bowel dysfunction, colic, vomiting or nausea or a combination thereof, particularly postoperative or postpartum ileus, opioid bowel dysfunction, postoperative nausea, or postoperative vomiting.

In other embodiments, the invention is directed to methods of preventing or treating pain in a patient, comprising the step of:
administering to said patient in need thereof an effective amount of the above-described composition.

In preferred embodiments, the composition further comprises at least one opioid.

In yet other embodiments, the invention is directed to kits, comprising:

a. a container comprising an injectable dosage formulation; and b. instructions for preparing an injectable solution.

Preferably, the kit further comprises a syringe. Preferably, the injectable dosage formulation further comprises at least one opioid. The composition may optionally comprise conventional pharmaceutical kit components.

The present invention is directed to methods, compositions, and kits involving opioid compounds. As discussed above, such opioid compounds may be useful, for example, in the treatment and/or prevention of pain. However, as also discussed above, undesirable side effects including, for example, ileus, pruritus, constipation, urinary retention, biliary spasm, opioid bowel dysfunction, colic, vomiting or nausea or a combination thereof, especially postoperative and postpartum ileus, opioid bowel dysfunction, nausea and/or vomiting, as well as other side effects, may frequently occur in patients receiving opioid compounds. By virtue of the methods, compositions, and kits of the present invention, effective and desirable inhibition of undesirable side effects that may be associated with opioid compounds may be advantageously achieved. Accordingly, combination methods, compositions and kits, where opioids are combined or co-administered with suitable peripheral μ opioid antagonist compounds, may afford an efficacy advantage over the compounds and agents alone.

In this connection, as discussed above, patients are often administered opioids for the treatment, for example, of painful conditions. However, as noted above, undesirable side effects such as, for example, ileus, pruritus, constipation, urinary retention, biliary spasm, opioid bowel dysfunction, colic, vomiting, or nausea or a combination thereof, may result from opioid administration. These undesirable side effects may act as a limiting factor in connection with the amount of opioid that may be administered to the patient. That is, the amount of opioid capable of being administered to the patient may be limited due to the undesired occurrence of the aforementioned side effects. The limited amounts of opioid that may be administered to a patient may, in turn, result in a disadvantageously diminished degree of pain alleviation. The present combination methods and compositions may be used to advantageously increase the amount of opioid administered to a patient, thereby obtaining enhanced pain alleviation, while reducing, minimizing and/or avoiding undesirable side effects that may be associated with the opioid. The peripheral μ opioid antagonists employed in the methods and compositions of the present invention preferably have substantially no central nervous system activity and, accordingly, desirably do not affect the pain killing efficacy of the opioid.

While not intending to be bound by any theory or theories of operation, it is contemplated that opioid side effects, such as ileus, pruritus, constipation, urinary retention, biliary spasm, opioid bowel dysfunction, colic, vomiting or nausea or a combination thereof, may result from undesirable interaction of the opioid with peripheral μ receptors. Administration of a peripherally-acting μ opioid antagonist according to the methods of the present invention may block interaction of the opioid compounds with the μ receptors, thereby preventing and/or inhibiting the side effects, in particular postoperative or postpartum ileus, opioid bowel dysfunction, nausea and/or vomiting.

Other μ opioid antagonist compounds that may be employed in the methods and compositions of the present invention, in addition to those exemplified above, would be readily apparent to one of ordinary skill in the art, once armed with the teachings of the present disclosure.

The compounds employed in the methods of the present invention may exist in prodrug form. As used herein, "prodrug" is intended to include any covalently bonded carriers that release the active parent drug, for example, as according to formulas I, employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As discussed in detail above, compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991.

The 4-aryl-piperidine derivatives of formula I of the present invention may be synthesized employing methods taught, for example, in U.S. Pat. No. 5,250,542, U.S. Pat. No. 5,434,171, U.S. Pat. No. 5,159,081, U.S. Pat. No. 5,270,328, U.S. Pat. No. 6,451,806, U.S. Pat. No. 6,469,030, and Werner, J. A., et al., *Journal of Organic Chemistry*, 61, 587-597 (1996), the disclosures of which are hereby incorporated herein by reference in their entireties. For example, the 3-substituted-4-methyl-4-(3-hydroxy- or alkanoyloxyphenyl)piperidine derivatives employed as starting materials in the synthesis of the present compounds may be prepared by the general procedure taught in U.S. Pat. No. 4,115,400 and U.S. Pat. No. 4,891,379, the disclosures of which are hereby incorporated herein by reference in their entireties. The starting material for the synthesis of compounds described herein, (3R,4R)-4-(3-hydroxyphenyl)-3,4-dimethylpiperidine, may be prepared by the procedures described in U.S. Pat. No. 4,581,456 and U.S. Pat. No. 5,136,040, the disclosures of which are hereby incorporated herein by reference, in their entirety, but adjusted as described such that the ∃-stereochemistry is preferred.

The first step of the process may involve the formation of the 3-alkoxyphenyllithium reagent by reacting 3-alkoxybromobenzene with an alkyllithium reagent. This reaction may be performed under inert conditions and in the presence of a suitable non-reactive solvent such as dry diethyl ether or preferably dry tetrahydrofuran. Preferred alkyllithium reagents used in this process are n-butyl lithium, and especially sec-butyl lithium. Generally, approximately an equimolar to slight excess of alkyllithium reagent may be added to the reaction mixture. The reaction may be conducted at a temperature of from about −20° C. and about −100° C., more preferably from about −50° C. to about −55° C.

Once the 3-alkoxyphenyllithium reagent has formed, approximately an equimolar quantity of a 1-alkyl-4-piperidone may be added to the mixture while maintaining the temperature between −20° C. and −100° C. The reaction is typically complete after about 1 to 24 hours. At this point, the reaction mixture may be allowed to gradually warm to room temperature. The product may be isolated by the addition to the reaction mixture of a saturated sodium chloride solution to quench any residual lithium reagent. The organic layer may be separated and further purified if desired to provide the appropriate 1-alkyl-4-(3-alkoxyphenyl)piperidinol derivative.

The dehydration of the 4-phenylpiperidinol prepared above may be accomplished with a strong acid according to well known procedures. While dehydration occurs in various amounts with any one of several strong acids such as hydrochloric acid, hydrobromic acid, and the like, dehydration is preferably conducted with phosphoric acid, or especially p-toluenesulfonic acid in toluene or benzene. This reaction may be typically conducted under reflux conditions, more generally from about 50° C. and 150° C. The product thus formed may be isolated by basifying an acidic aqueous solution of the salt form of the product and extracting the aqueous solution with a suitable water immiscible solvent. The resulting residue following evaporation can then be further purified if desired.

The 1-alkyl-4-methyl-4-(3-alkoxyphenyl)tetrahydropyridine derivatives may be prepared by a metalloenamine alkylation. This reaction is preferably conducted with n-butyl lithium in tetrahydrofuran (THF) under an inert atmosphere, such as nitrogen or argon. Generally, a slight excess of n-butyl lithium may be added to a stirring solution of the 1-alkyl-4-(3-alkoxyphenyl)-tetrahydropyridine in THF cooled to a temperature in the range of from about −50° C. to about 0° C., more preferably from about −20° C. to −10° C. This mixture may be stirred for approximately 10 to 30 minutes followed by the addition of approximately from 1.0 to 1.5 equivalents of methyl halide to the solution while maintaining the temperature of the reaction mixture below 0° C. After about 5 to 60 minutes, water may be added to the reaction mixture and the organic phase may be collected. The product can be purified according to standard procedures, but the crude product is preferably purified by either distilling it under vacuum or slurrying it in a mixture of hexane:ethyl acetate (65:35, v:v) and silica gel for about two hours. According to the latter procedure, the product may be then isolated by filtration followed by evaporating the filtrate under reduced pressure.

The next step in the process may involve the application of the Mannich reaction of aminomethylation to non-conjugated, endocyclic enamines. This reaction is preferably carried out by combining from about 1.2 to 2.0 equivalents of aqueous formaldehyde and about 1.3 to 2.0 equivalents of a suitable secondary amine in a suitable solvent. While water may be the preferred solvent, other non-nucleophilic solvents, such as acetone and acetonitrile can also be employed in this reaction. The pH of this solution may be adjusted to approximately 3.0 to 4.0 with an acid that provides a non-nucleophilic anion. Examples of such acids include sulfuric acid, the sulfonic acids such as methanesulfonic acid and p-toluenesulfonic acid, phosphoric acid, and tetrafluoroboric acid, with sulfuric acid being preferred. To this solution may be added one equivalent of a 1-alkyl-4-methyl-4-(3-alkoxyphenyl)tetrahydropyridine, typically dissolved in aqueous sulfuric acid, and the pH of the solution may be readjusted with the non-nucleophilic acid or a suitable secondary amine. The pH is preferably maintained in the range of from about 1.0 to 5.0, with a pH of about 3.0 to 3.5 being more preferred during the reaction. The reaction is substantially complete after about 1 to 4 hours, more typically about 2 hours, when conducted at a temperature in the range of from about 50° C. to about 80° C., more preferably about 70° C. The reaction may then be cooled to approximately 30° C., and added to a sodium hydroxide solution. This solution may then be extracted with a water immiscible organic solvent, such as hexane or ethyl acetate, and the organic phase, following thorough washing with water to remove any residual formaldehyde, may be evaporated to dryness under reduced pressure.

The next step of the process may involve the catalytic hydrogenation of the prepared 1-alkyl-4-methyl-4-(3-alkoxyphenyl)-3-tetrahydropyridinemethanamine to the corresponding trans-1-alkyl-3,4-dimethyl-4-(3-alkoxyphenyl)piperidine. This reaction actually occurs in two steps. The first step is the hydrogenolysis reaction wherein the exo C—N bond is reductively cleaved to generate the 3-methyltetrahydropyridine. In the second step, the 2,3-double bond in the tetrahydropyridine ring is reduced to afford the desired piperidine ring.

Reduction of the enamine double bond introduced the crucial relative stereochemistry at the 3 and 4 carbon atoms of the piperidine ring. The reduction generally does not occur with complete stereoselectivity. The catalysts employed in the process may be chosen from among the various palladium and preferably platinum catalysts.

The catalytic hydrogenation step of the process is preferably conducted in an acidic reaction medium. Suitable solvents for use in the process include the alcohols, such as methanol or ethanol, as well as ethyl acetate, tetrahydrofuran, toluene, hexane, and the like.

Proper stereochemical outcome may be dependent on the quantity of catalyst employed. The quantity of catalyst required to produce the desired stereochemical result may be dependent upon the purity of the starting materials in regard to the presence or absence of various catalyst poisons.

The hydrogen pressure in the reaction vessel may not be critical but can be in the range of from about 5 to about 200 psi. Concentration of the starting material by volume is preferably about 20 mL of liquid per gram of starting material, although an increased or decreased concentration of the starting material can also be employed. Under the conditions specified herein, the length of time for the catalytic hydrogenation may not be critical because of the inability for over-reduction of the molecule. While the reaction can continue for up to about 24 hours or longer, it may not be necessary to continue the reduction conditions after the uptake of the theoretical two moles of hydrogen. The product may then be isolated by filtering the reaction mixture for example through infusorial earth, and evaporating the filtrate to dryness under reduced pressure. Further purification of the product thus isolated may not be necessary and preferably, the diastereomeric mixture may be carried directly on to the following reaction.

The alkyl substituent may be removed from the 1-position of the piperidine ring by standard dealkylation procedures. Preferably, a chloroformate derivative, especially the vinyl or phenyl derivatives, may be employed and removed with acid. Next, the prepared alkoxy compound may be dealkylated to the corresponding phenol. This reaction may be generally carried out by reacting the compound in a 48% aqueous hydrobromic acid solution. This reaction may be substantially complete after about 30 minutes to about 24 hours when conducted at a temperature of from about 50° C. to about 150° C., more preferably at the reflux temperature of the reaction mixture. The mixture may then be worked up by cooling the solution, followed by neutralization with base to an approximate pH of 8. This aqueous solution may be extracted with a water immiscible organic solvent. The residue following evaporation of the organic phase may then be used directly in the following step.

The compounds employed as starting materials to the compounds of the invention can also be prepared by brominating the 1-alkyl-4-methyl-4-(3-alkoxyphenyl)-3-tetrahydropyridinemethanamine at the 3-position, lithiating the bromo compound thus prepared, and reacting the lithiated intermediate with a methylhalide, such as methyl bromide to provide the corresponding 1-alkyl-3,4-dimethyl-4-(3-alkoxyphenyl) tetrahydropyridinemethanamine. This compound may then be reduced and converted to the starting material as indicated above.

As noted above, the compounds of the present invention can exist as the individual stereoisomers. Preferably, reaction conditions are adjusted as disclosed in U.S. Pat. No. 4,581,456 or as set forth in Example 1 of U.S. Pat. No. 5,250,542 to be substantially stereoselective and provide a racemic mixture of essentially two enantiomers. These enantiomers may then be resolved. A procedure which may be employed to prepare the resolved starting materials used in the synthesis of these compounds includes treating a racemic mixture of alkyl-3,4-dimethyl-4-(3-alkoxyphenyl)piperidine with either (+)- or (−)-ditoluoyl tartaric acid to provide the resolved intermediate. This compound may then be dealkylated at the 1-position with vinyl chloroformate and finally converted to the desired 4-(3-hydroxyphenyl)piperidine isomer.

Alternatively, the stereoselective syntheses of 3,4-alkyl-substituted-4-(3-hydroxyphenyl)piperidines could be performed by the methods described by Werner, J. A., et al., *Journal of Organic Chemistry*, 61, 587-597 (1996) and U.S. Pat. No. 5,136,040 using alkoxyphenyllithium (−20° C. to −100° C.) or the corresponding Grignard reagents (40° C. to 60° C.) and 1,3-dialkyl-4-piperidone.

Acylation of the resulting alcohol with ethyl chloroformate gave the racemic carobante which was efficiently resolved with (+)-di-p-toluoyl-D-tartaric acid (DTTA). Thermal elimination (170-200° C.) of freebase of the chirally pure carbonate gave the desired olefin.

For example, methylation of the olefin with dimethyl sulfate in presence of n-butyl lithium gave the trans-3,4-dimethyl enamine. The reduction of enamine with sodium borohydride followed by purification (+)-DTTA gave the compound with enantiomeric purity >99.5%. Demethylation of the free base with phenyl chloroformate followed by removal of protecting groups resulted in the (3R,4R)-3-(3,4-dimethyl-4-piperidinyl)phenol, a key intermediate for the preparation of compounds of formula I. Alvimopan is manufactured by the process described in *Journal of Organic Chemistry*, 61, 587-597 (1996) and U.S. Pat. No. 5,136,040.

As will be understood by those skilled in the art, the individual enantiomers of the invention can also be isolated with either (+) or (−) dibenzoyl tartaric acid, as desired, from the corresponding racemic mixture of the compounds of the invention. Preferably, the (+)-trans enantiomer is obtained.

Although the (+)trans-3,4 stereoisomer is preferred, all of the possible stereoisomers of the compounds described herein are within the contemplated scope of the present invention. Racemic mixtures of the stereoisomers as well as the substantially pure stereoisomers are within the scope of the invention. The term "substantially pure," as used herein, refers to at least about 90 mole percent, more preferably at least about 95 mole percent and most preferably at least about 98 mole percent of the desired stereoisomer is present relative to other possible stereoisomers.

Intermediates can be prepared by reacting a 3,4-alkyl-substituted-4-(3-hydroxyphenyl)piperidine with a compound of the formula $LCH_2(CH_2)_{n-1}CHR^3C(O)E$ where L is a leaving group such as chlorine, bromine or iodine, E is a carboxylic acid, ester or amide, and $R^3$ and n are as defined hereinabove. Preferably, L may be chlorine and the reaction is carried out in the presence of a base to alkylate the piperidine nitrogen. For example 4-chloro-2-cyclohexylbutanoic acid, ethyl ester can be contacted with (3R,4R)-4-(3-hydroxyphenyl)-3,4-dimethylpiperidine to provide 4-[(3R,4R)-4-(3-hydroxyphenyl)-3,4-dimethyl-1-piperidine]butanoic acid, ethyl ester. Although the ester of the carboxylic acid may be preferred, the free acid itself or an amide of the carboxylic acid may be used.

In alternative synthesis, the substituted piperidine can be contacted with a methylene alkyl ester to alkylate the piperidine nitrogen. For example, 2-methylene-3-phenylproponic acid, ethyl ester can be contacted with a desired piperidine to provide 2-benzyl-3-piperidinepropanoic acid ethyl ester.

Another synthetic route can involve the reaction of a substituted piperidine with a haloalkylnitrile. The nitrile group of the resulting piperidine alkylnitrile can be hydrolyzed to the corresponding carboxylic acid.

With each of the synthetic routes, the resulting ester or carboxylic acid can be reacted with an amine or alcohol to provide modified chemical structures. In the preparation of amides, the piperidine-carboxylic acid or piperidine-carboxylic acid ester may be reacted with an amine in the presence of a coupling agent such as dicyclohexylcarbodiimide, boric acid, borane-trimethylamine, and the like. Esters can be prepared by contacting the piperidine-carboxylic acid with the appropriate alcohol in the presence of a coupling agent such as p-toluenesulfonic acid, boron trifluoride etherate or N,N'-carbonyldiimidazole. Alternatively, the piperidine-carboxylic acid chloride can be prepared using a reagent such as thionyl chloride, phosphorus trichloride, phosphorus pentachloride and the like. This alkanoyl chloride can be reacted with the appropriate amine or alcohol to provide the corresponding amide or ester.

The compounds of formula I are combined with a pharmaceutical acceptable bulking agent selected on the basis of the chosen route of administration and standard pharmaceutical practice as described, for example, in *Remington's Pharma-*

*ceutical Sciences* (Mack Publishing Co., Easton, Pa., 1980), the disclosures of which is hereby incorporated herein by reference, in its entirety.

Compounds of formula I can be administered to a mammalian host in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

The amount of active compound(s) in such therapeutically useful compositions is preferably such that a suitable dosage will be obtained. Preferred compositions or preparations according to the present invention may be prepared so that a dosage unit form contains from about 0.1 to about 1000 mg of active compound, more preferable from about 1 to 100 mg of the active compound.

Based on the intended use, these preparations may contain a preservative to prevent the growth of microorganisms.

The pharmaceutical forms suitable for injectable use include, for example, sterile aqueous solutions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The prevention of the action of microorganisms may be achieved by various antibacterial and antifungal agents, for example, parabens, chlorobutanol, phenol, sorbic acid, thimerosal and the like.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders or cake for the preparation of sterile injectable solutions, the preferred methods of preparation may include spray drying, vacuum drying, and freeze-drying (lyophilization) techniques that yield a powder of the active ingredient, plus any additional desired ingredient from the previously sterile-filtered solution thereof.

The composition of the invention may be orally administered. For example, the dried composition of the invention may be enclosed in hard or soft shell gelatin capsules, it may be compressed into tablets (such as fast-dissolve oral tablets, oral disintegrating tablets, including those for buccal administration), or it may be incorporated directly with the food of the diet.

The tablets, troches, pills, capsules and the like for oral administration may also contain one or more of the following provided that they do not interfere with improved solubility and bioavailability of the composition: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

As noted above, the relative proportions of active ingredient and carrier may be determined, for example, by the solubility and chemical nature of the compounds, chosen route of administration, and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached.

The combination products of this invention, such as pharmaceutical compositions comprising opioids in combination with a peripheral μ opioid antagonist compound, such as the compounds of formula I, may be in any parenteral dosage form, such as those described herein, and can also be administered in various ways, as described herein. In a preferred embodiment, the combination products of the invention are formulated together, in a single dosage form (that is, combined together in one liquid, etc.). When the combination products are not formulated together in a single dosage form, the opioid compounds and the peripheral μ opioid antagonist compounds may be administered at the same time or simultaneously (that is, together), or in any order. When not administered at the same time or simultaneously, that is, when administered sequentially, preferably the administration of a peripheral μ opioid antagonist and opioid occurs less than about one hour apart, more preferably less than about 30 minutes apart, even more preferably less than about 15 minutes apart, and still more preferably less than about 5 minutes apart.

Although it is preferable that the peripheral μ opioid antagonists and opioids are administered in the same fashion (that is, for example, both parenterally), if desired, they may each be administered in different fashions (that is, for example, the opioid component of the combination product may be administered orally, and peripheral μ opioid antagonist component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Although the proper dosage of the combination products of this invention will be readily ascertainable by one skilled in the art, once armed with the present disclosure, by way of general guidance, where an opioid compounds is combined with a peripheral μ opioid antagonist, for example, typically a daily dosage may range from about 0.01 to about 100 milligrams of the opioid (and all combinations and subcombinations of ranges therein) and about 0.001 to about 100 milligrams of the peripheral μ opioid antagonist (and all combinations and subcombinations of ranges therein) per kilogram of patient body weight. Preferably, the a daily dosage may be about 0.1 to about 10 milligrams of the opioid and about 0.01 to about 10 milligrams of the peripheral μ opioid antagonist per kilogram of patient body weight. Even more preferably, the daily dosage may be about 1.0 milligrams of the opioid and about 0.1 milligrams of the peripheral μ opioid antagonist per kilogram of patient body weight. With regard to a typical dosage form of this type of combination product, the opioid compounds (e.g., morphine) generally may be present in an amount of about 5 to about 200 milligrams and the peripheral μ opioid antagonists in an amount of about 0.1 to about 12 milligrams.

Pharmaceutical kits useful in, for example, the treatment of the side effects of opioid administration or treatment of pain, which comprise a therapeutically effective amount of an opioid along with a therapeutically effective amount of a peripheral μ opioid antagonist compound, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The optional opioid compound and the peripheral μ opioid antagonist compound may be separate, or combined into a single dosage form as described above. Such kits may further include, if desired, one or more of various conventional pharmaceutical kit components, such as for example, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Compounds for use in the methods, compositions, and kits of the present invention, including the compounds of formula I, have been characterized in opioid receptor binding assays showing preferential binding to μ opioid receptors. Studies in isolated tissues (guinea pig ileum and mouse vas deferens) and in other in vitro systems (e.g., GTPγS) have shown that these compounds may act as antagonists with no measurable agonist activity. Studies in animals have demonstrated that the present compounds may reverse constipation in morphine-dependent mice when administered orally or parenterally at very low doses, and do not block the analgesic actions of morphine unless given in hundred-fold or higher doses. Collectively, the data indicate that the compounds described herein may have a very high degree of peripheral selectivity.

EXAMPLES

The present invention will now be illustrated by reference to the following specific, non-limiting examples. The examples are not intended to limit the scope of the present invention.

Example 1

Synthesis of Alvimopan

Alvimopan was prepared in accordance with the following synthetic procedure.

Synthesis of 1-bromo-3-(1-methylethoxy)benzene (Compound 1)

| Reagent | MW | Amount (kg) | Kilomoles | Molar Ratio |
|---|---|---|---|---|
| 3-Bromophenol | 173.01 | 80.0 | 0.4624 | 1.00 |
| 2-Bromopropane | 123.0 | 85.6 | 0.6959 | 1.51 |
| Potassium carbonate, ground | 138.2 | 96.0 | 0.6946 | 1.50 |
| Ethanol 1X * | 46.07 | 144 | — | — |
| Water | 18.02 | 739 | — | — |
| Hydrochloric acid, 31% | 36.46 | 6.6 | — | — |
| Sodium hydroxide, 50% w/w | 40.0 | 44.4 | — | — |
| Heptanes | 100.2 | 185 | — | — |

* Ethanol 1X was denatured with 0.5% toluene.

A reactor was charged with ground potassium carbonate (96.0 kg) and ethanol 1X (134 kg). The reaction mixture was adjusted to 20 to 25° C.

With agitation, 3-bromophenol (80.0 kg) was charged to the reactor while maintaining the temperature between 20 to 35° C. The transfer equipment was rinsed forward with ethanol 1X (5 kg). The temperature was adjusted to 20 to 25° C. 2-Bromopropane (85.6 kg) was charged to the reactor. The transfer equipment was rinsed forward with ethanol 1X (5 kg). Water (20 L) was charged to the reactor.

The solution in the reactor was heated to 60 to 65° C. and maintained in that range for a minimum of 16 hours. The mixture was cooled to 45 to 50° C. and the mixture was verified for 3-bromophenol. The mixture was warmed to 60 to 65° C. while awaiting the results. The mixture was cooled to 45 to 50° C. once more.

Water (303 L) was charged to the reactor. The reaction mixture was reduced to a concentrate volume of 400 L via atmospheric distillation. The concentrated mixture was cooled to 20 to 25° C.

Heptanes (185 kg) were charged to the reactor and then stirred at a temperature of 20 to 25° C. for a minimum of 20 minutes.

The biphasic solution was separated and the organic layer was washed with a solution of water (45 L) and hydrochloric acid, 31% (6.6 kg). The organic layer was washed with water (56 L) followed by a solution of water (49 L) and sodium hydroxide, 50% (4.4 kg). The organic layer was washed one final time with water (56 L).

The organic solution was dried via azeotropic distillation until no more water was collected. The reaction mixture was then reduced to a concentrate volume of 150 to 170 L via atmospheric distillation and cooled to 20 to 25° C. The solution was packaged for use in the next step. The packaged product (Compound 1) was sampled, tested: HPLC purity not less than 98% a/a and HPLC assay not less than 55% w/w.

Synthesis of cis-(±)-1,3-dimethyl-4-[3-(1-methyl-ethoxy)phenyl]-4-piperidinol (Compound 2)

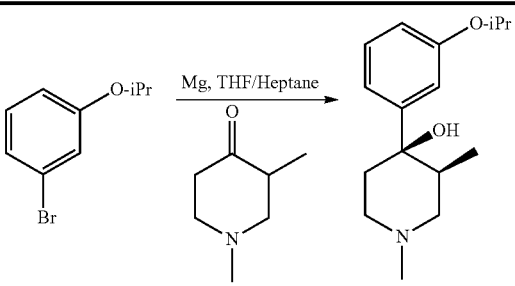

| Reagent | MW | Amount (kg) | Kilomoles | Molar Ratio |
|---|---|---|---|---|
| Compound 1 | 215.1 | 27.9 | 0.07514* | 1.21 |
| Magnesium turnings | 24.3 | 2.1 | 0.08642 | 1.39 |
| 1,3-Dimethyl-4-piperidone | 127.2 | 7.9 | 0.06211 | 1.00 |
| Tetrahydrofuran | 72.01 | 162 | — | — |
| Ammonium chloride | 53.5 | 6.6 | — | — |
| Water | 18.02 | 56 | — | — |
| Hyflo supercel | — | 4 | — | — |
| Heptanes | 100.2 | 86.5 | — | — |

*Calculated as per assay of reagent

The tetrahydrofuran to be used was sampled for water content prior to use in the lot.

A reactor was charged with tetrahydrofuran (18 kg) and heated to reflux without agitation. The solvent was maintained at reflux for 1 hour and cooled to 30° C. or less. A KF analysis was performed to ensure that the amount of water in the reactor meets the specifications. The THF was drained to waste and the reactor was dried.

Magnesium (2.1 kg) was charged to the reactor, followed by tetrahydrofuran (80 kg). With agitation, the reaction mixture was reduced to a concentrate volume of 40 to 44 L via atmospheric distillation. The concentrate was cooled to 40 to 45° C.

A portable agitation stainless steel tank was charged with tetrahydrofuran (18 kg) and agitated for a minimum of 20 minutes. A KF analysis was performed to ensure that the amount of water in the reactor meets the specifications. The THF was drained to waste.

The tank was charged with 1-bromo-3-(1-methylethoxy) benzene (27.9 kg) and tetrahydrofuran (31 kg). The solution was agitated at room temperature for a minimum of 20 minutes.

A 2.5 kg portion of the mixture in the tank was transferred into the reactor starting at a temperature of 40 to 45° C. With agitation, the mixture was maintained at 40 to 60° C. for a minimum of 30 minutes.

A second 2.5 kg portion of the mixture in the tank was transferred into the reactor starting at a temperature of 40 to 45° C. With agitation, the mixture was maintained at 40 to 60° C. for a minimum of 30 minutes.

A 5 kg portion of the mixture in the tank was transferred into the reactor starting at a temperature of 40 to 45° C. With agitation, the mixture was maintained at 40 to 60° C. for a minimum of 30 minutes.

The tank was charged with 1,3-dimethyl-4-piperidone (7.9 kg) and the transfer equipment was rinsed forward with tetrahydrofuran (5 kg).

A 15 kg portion of the mixture in the tank was transferred into the reactor over a minimum of 1 hour, starting at a temperature of 40 to 45° C. With agitation, the mixture was maintained at 40 to 60° C. for 15 to 30 minutes. The reaction mixture was cooled to 40 to 45° C.

A second 15 kg portion of the mixture in the tank was transferred into the reactor over a minimum of 1 hour, starting at a temperature of 40 to 45° C. With agitation, the mixture was maintained at 40 to 60° C. for 15 to 30 minutes. The reaction mixture was cooled to 40 to 45° C.

A third 15 kg portion of the mixture in the tank was transferred into the reactor over a minimum of 1 hour, starting at a temperature of 40 to 45° C. With agitation, the mixture was maintained at 40 to 60° C. for 15 to 30 minutes. The reaction mixture was cooled to 40 to 45° C.

The remainder of the mixture in the tank was transferred into the reactor over a minimum of 1 hour, starting at a temperature of 40 to 45° C. The transfer equipment was rinsed forward with THF (5 kg). With agitation, the mixture was maintained at 40 to 60° C. for 15 to 30 minutes. The mixture was cooled to 40 to 45° C.

After the reaction was complete, the mixture was cooled to 20 to 25° C.

A second reactor was charged with water (40 L) and ammonium chloride (6.6 kg). With moderate agitation, the mixture was maintained at 20 to 25° C. for a minimum of 20 minutes.

Once the solids have dissolved, Hyflo supercel (4 kg) was charged into the second reactor. The aqueous mixture was cooled to 0 to 5° C.

With agitation, the organic mixture in the first reactor was transferred through to the second reactor. The transfer equipment was rinsed forward with THF (5 kg). The mixture was warmed to 20 to 25° C. and maintained for a minimum of 15 minutes.

The mixture was filtered into the first reactor, rinsed forward with heptanes (2×6 kg), and maintained at 20 to 25° C. for a minimum of 20 minutes.

The biphasic solution was separated and the organic layer was washed with water (16 L). The organic solution was reduced to a concentrate volume of 30 to 34 L via atmospheric distillation and cooled to 45 to 50° C.

Heptanes (54 kg) was charged to the reactor and the solution was reduced to a concentrate volume of 69 to 73 L via atmospheric distillation. The solution was cooled to 30 to 35° C. The reaction mixture was verified for residual tetrahydrofuran and water content. Reaction was seeded with crystals of the product and the mixture was cooled to 0 to 5° C. over a minimum of 1 hour and maintained for a minimum of 3 hours.

The solid product was isolated via filtration, washed with cold heptanes (2×10 kg) and dried. The product was sampled for dryness and packaged. The packaged product (Compound 2) was sampled, tested: HPLC purity not less than 97% a/a and released prior to use in the next step.

Purification of cis-(±)-1,3-dimethyl-4-[3-(1-methylethoxy)phenyl]-4-piperidinol (Compound 2)

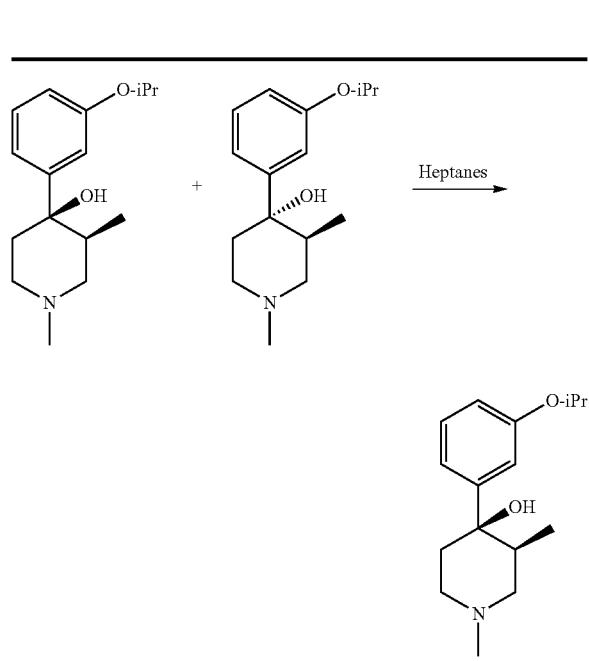

| Reagent | MW | Amount (kg) | Kilomoles | Molar Ratio |
|---|---|---|---|---|
| Compound 2 | 263.4 | 96.1 | 0.3648 | 1.00 |
| Heptanes | 100.2 | 590 | — | — |

A reactor was charged with compound 2 (96.1 kg) and heptanes (328 L). The mixture was heated to 55 to 60° C. and maintained for a minimum of 1 hour. The mixture was verified to ensure that all of the solids have dissolved.

The solution was cooled to 30 to 35° C. over a minimum of 1 hour and maintained for a minimum of 1 hour. The mixture was verified to ensure that precipitation has occurred. The mixture was cooled to 0 to 5° C. over a minimum of two hours and maintained for a minimum of 4 hours.

The solid purified compound 2 was isolated via filtration, washed with cold heptanes (2×131 kg) and dried. The product was sampled for dryness and packaged. The packaged product was sampled, tested for HPLC purity, not less than 97% a/a and released prior to use in the next step.

Synthesis of carbonic acid, ethyl (3S,4R)-1,3-dimethyl-4-[3-(1-methylethoxy) phenyl]-4-piperidinyl ester compound with (+)-D-2,3-bwas[(4-methylbenzoyl)oxy]butanedioic acid (1:1) (Compound 3)

| Reagent | MW | Amount (kg) | Kilomoles | Molar Ratio |
|---|---|---|---|---|
| Compound 2 | 263.4 | 10.8 | 0.04100 | 1.00 |
| Ethyl chloroformate | 108.52 | 5.6 | 0.05160 | 1.26 |
| Triethylamine, anhydrous | 101.19 | 0.4 | 0.003953 | 0.10 |
| (+) DTTA | 386.36 | 15.8 | 0.04089 | 1.00 |
| Sodium hydroxide, 50% w/w | 40.0 | 47.6 | — | — |
| Ethyl acetate | 88.11 | 52 | — | — |
| Ethanol 1X | 46.07 | 285 | — | — |

A reactor was charged with compound 2 (10.8 kg) and ethyl acetate (48 kg). The mixture was maintained at 20 to 25° C. for a minimum of 30 minutes until all of the solids have dissolved. The solution was cooled to 0 to 5° C.

Triethylamine (0.4 kg) was charged to the reactor and the transfer equipment was rinsed forward with ethyl acetate (1 kg).

Ethyl chloroformate (5.6 kg) was charged to the reactor while maintaining a temperature of 0 to 15° C. The transfer equipment was rinsed forward with ethyl acetate (3 kg). The mixture was maintained at 20 to 25° C. for a minimum of 3 hours.

Sodium hydroxide, 50% (7.6 kg) was charged to the reactor while maintaining a temperature of 0 to 38° C. The transfer equipment was rinsed forward with water (17 L). The solution was maintained at 20 to 25° C. for a minimum of 20 minutes and the pH of the solution was checked to ensure it was above 10.

The biphasic solution was separated and the organic layer was washed twice with water (22 L). The organic solution was dried via azeotropic distillation, and then reduced to a concentrate volume of 20 to 24 L via atmospheric distillation. The solution was cooled to 40 to 50° C.

Ethanol 1X (60 kg) was charged to the reactor. The solution was reduced to a concentrate volume of 30 to 34 L via atmospheric distillation and cooled to 55 to 60° C.

A glass-lined reactor was charged with (+)-di-p-toluoyl-D-tartaric acid (15.8 kg) and ethanol 1X (51 kg). With moderate agitation, the temperature was adjusted to 60 to 65° C.

The reaction mixture was transferred into the acid solution while maintaining a temperature of 60 to 70° C. The transfer equipment was rinsed forward with ethanol 1X (17 kg). The solution was maintained at 60 to 65° C. for a period of 1 to 1.5 hours. The suspension was cooled to 50 to 55° C. and maintained for a period of 2 to 2.5 hours. The suspension was cooled to 20 to 25° C. over a minimum of 3 hours and maintained for a minimum of 10 hours.

The solid was isolated by filtration, washed with ethanol 1X (17 kg), dried and packaged. The packaged crude product was sampled and tested for chiral purity of compound 3.

A reactor was charged with the crude product and ethanol 1X (as per calculation). The mixture was adjusted to 60 to 65° C. and maintained for a period of 2 to 2.5 hours. The suspension was cooled to 20 to 25° C. over a minimum of 2 hours. The suspension was cooled to 0 to 5° C. and maintained for a minimum of 3 hours.

The solid compound 3 was isolated via filtration, washed with cold ethanol 1X (17 kg), dried and packaged. The packaged product was sampled, tested, HPLC purity not less than 99.0% a/a; Chiral HPLC, not less than 99.5% and released prior to use in the next step.

Synthesis of (3R,4R)-3-(3,4-dimethyl-4-piperidinyl)phenol (Compound 4)

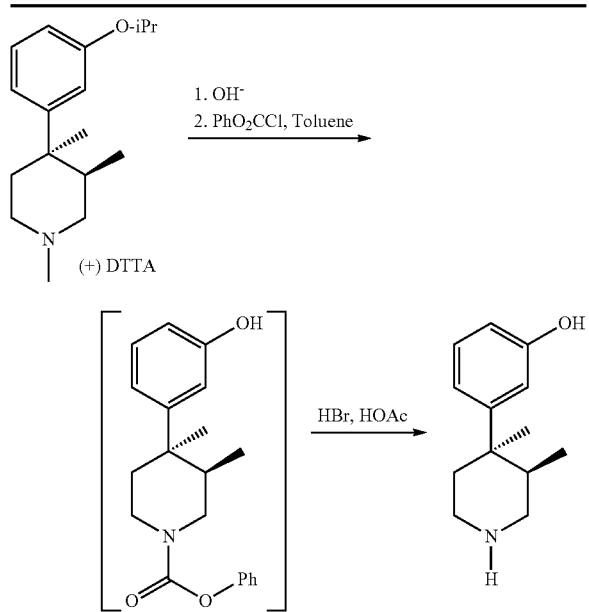

| Reagent | MW | Amount (kg) | Kilomoles | Molar Ratio |
|---|---|---|---|---|
| Compound 3 | 647.8 | 18.3 | 0.02825 | 1.00 |
| Toluene | 92.14 | 50 | — | — |
| Water | 18.02 | 434 | — | — |
| Sodium hydroxide, 50% w/w | 40.0 | 110.7 | — | — |
| Phenyl chloroformate | 156.57 | 5.3 | 0.03385 | 1.20 |
| Hydrochloric acid, 31% | 36.46 | 2.8 | — | — |
| Acetic acid, glacial | 60.05 | 17.6 | 0.2931 | 10.38 |
| Hydrobromic acid | 80.92 | 19 | 0.1127 | 4.00 |
| t-Butyl methyl ether | 88.15 | 56 | — | — |
| Methanol | 32.04 | 8.7 | — | — |

A reactor was charged with compound 3 (18.3 kg), toluene (48 kg), and water (32 L). The mixture was adjusted to 20 to 25° C.

Sodium hydroxide, 50% (9.2 kg) was charged to the reactor while maintaining a temperature of 20 to 30° C. The transfer equipment was rinsed forward with water (4 L). With agitation, the mixture was cooled to 20 to 25° C. and maintained for 1 hour. The pH of the aqueous layer was checked to ensure that it was above 12.

The biphasic solution was separated and the organic layer was washed with a solution of water (14 L) and sodium hydroxide, 50% (0.7 kg). The organic layer was washed twice with water (15 L) and dried via azeotropic distillation. The solution was cooled to 80 to 85° C.

Phenyl chloroformate (5.3 kg) was charged to the reactor over a minimum of 1.5 hours while maintaining a temperature of 80 to 85° C. The transfer equipment was rinsed forward with toluene (2 kg). The solution was heated to reflux and maintained for a minimum of 3 hours, then cooled to 50 to 55° C. The mixture was maintained at reflux while awaiting the results.

The mixture was cooled to 20 to 25° C. and water (14 L) was charged to the reactor. Sodium hydroxide, 50% (2.3 kg) was charged to the reactor over a minimum of 1 hour while maintaining a temperature of 20 to 30° C. The transfer equipment was rinsed forward with water (4 L). The solution was maintained at 20 to 25° C. for a minimum of 1 hour.

The biphasic solution was separated and the organic layer was washed with a solution of water (15 L) and hydrochloric acid, 31% (1.9 kg). The organic solution was reduced to a concentrate volume of 23 to 26 L via atmospheric distillation and cooled to 65 to 70° C.

Water (7 L) and acetic acid (13.6 kg) were charged to the reactor. The transfer equipment was rinsed forward with water (2 L). The solution was reduced to a concentrate volume of 26 to 29 L via atmospheric distillation and cooled to 50 to 60° C.

Hydrobromic acid (19 kg) was charged to the reactor, followed by acetic acid (4 kg). The solution was heated to reflux and maintained for a minimum of 18 hours. The solution was cooled to 55 to 60° C. The solution was cooled to 10 to 15° C.

Sodium hydroxide, 50% (6 kg) was charged to the reactor over a minimum of 1 hour while maintaining a temperature of 10 to 30° C. The transfer equipment was rinsed forward with water (5 L). The temperature was adjusted to 20 to 25° C. and the pH was checked to ensure it was less than 1.7.

To the reactor, t-butyl methyl ether (16 kg) was charged while maintaining a temperature of 20 to 25° C. Water (27 L) was charged to the reactor and the solution was maintained at 20 to 25° C. for a minimum of 30 minutes.

The biphasic solution was separated and the aqueous solution was transferred to a reactor. The organic solution was transferred to a 200 L glass receiver. The aqueous solution was washed twice with t-butyl methyl ether (16 kg).

The organic layers were transferred from the glass receiver to a reactor. Water (5 L) was charged to the reactor, followed by hydrochloric acid, 31% (0.9 kg) while maintaining a temperature of 20 to 25° C. The transfer equipment was rinsed forward with water (2 L). The biphasic solution was maintained at 20 to 25° C. for a minimum of 20 minutes.

The biphasic solution was separated and the aqueous solution was washed twice with t-butyl methyl ether (4 kg).

The acidic solution from the new PE drum was transferred to the 200 L reactor. The transfer equipment was rinsed forward with water (2 L).

Methanol (8.7 kg) was charged to the reactor over a minimum of 30 minutes while maintaining a temperature of 20 to 25° C.

A portable agitation stainless steel tank was charged with water (41 L) and sodium hydroxide, 50% (12.5 kg). The transfer equipment was rinsed forward with water (4 L). The solution was transferred to the reactor to achieve a pH of 10.0 to 10.5 while maintaining a temperature of 20 to 35° C.

The suspension was cooled to 0 to 5° C. and maintained for a minimum of 4 hours.

The compound 4 was isolated via filtration, washed with cold water (2×9 L), dried, and packaged. The packaged product was sampled, tested: HPLC Purity, not less than 98.5% a/a; Chiral Purity, not less than 99.0% and HPLC Assay, not less than 95% w/w and released prior to use in the next step.

Synthesis of methyl (αS,3R,4R)-4-(3-hydroxyphenyl)-3,4-dimethyl-α-(phenylmethyl)-1-piperidinepropanoate hydrochloride (Compound 6)

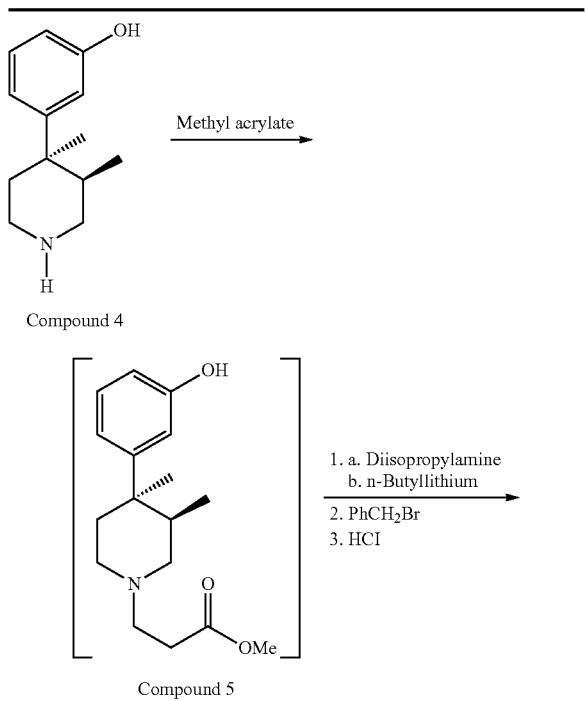

| Reagent | MW | Amount (kg) | Kilomoles | Molar Ratio |
|---|---|---|---|---|
| Compound 4 | 205.3 | 19.2 | 0.09352 | 1.00 |
| Methyl acrylate | 86.09 | 8.5 | 0.09875 | 1.05 |
| Tetrahydrofuran | 72.11 | 692 | — | — |
| n-Butyllithium | 64.06 | 87.4 | 0.2056 | 2.20 |
| Diisopropylamine | 101.19 | 21.8 | 0.2154 | 2.30 |
| Benzyl bromide | 171.04 | 32.0 | 0.1871 | 2.00 |
| Heptanes | 100.21 | 209 | — | — |
| Methanol | 32.04 | 659 | — | — |
| Hydrochloric acid, 31% | 36.46 | 36.2 | 0.3078 | 3.29 |
| Sodium hydroxide, 50% w/w | 40.0 | 4.9 | 0.06125 | 0.65 |
| Hydrogen chloride gas | 36.46 | 14.4 | 0.3950 | 4.23 |
| Hyflo supercel | — | 1.9 | — | — |
| Water | 18.02 | 566 | — | — |

A reactor was charged with compound 4 (19.2 kg) and tetrahydrofuran (222 kg). The mixture was heated to 40 to 45° C. with 50% agitation.

Methyl acrylate (8.5 kg) was charged to the reactor over a minimum of 30 minutes while maintaining a temperature of 40 to 45° C. The transfer equipment was rinsed forward with THF (17 kg). The reaction mixture was maintained at 40 to 45° C. for a period of 18 to 19 hours. The reaction mixture was cooled to 20 to 25° C.

A portable agitation stainless steel tank was charged with hyflo supercel (1.9 kg) and heptanes (13 kg). The mixture was agitated for a minimum of five minutes. The mixture was transferred to the reactor and rinsed forward with heptanes (5 kg). The mixture was maintained at 20 to 25° C. for a minimum of 20 minutes.

The mixture was filtered into a reactor for clarification, rinsed forward with heptanes (26 kg) and cooled to −5 to 0° C. The solution was reduced to a concentrate volume of 29 to 48 L via vacuum distillation to give a solution of compound 5.

Heptanes (26 kg) was charged to the reactor at 30° C. or less. The solution was cooled to −5 to 0° C. and reduced to a concentrate volume of 29 to 48 L via vacuum distillation.

Tetrahydrofuran (333 kg) was charged to the reactor, followed by diisopropylamine (21.8 kg). The transfer equipment was rinsed forward with tetrahydrofuran (12 kg). The solution was cooled to −15 to −10° C.

The reactor was charged with n-butyllithium in hexanes (87.4 kg) over a minimum of 1 hour while maintaining a temperature of −15 to −5° C. The transfer equipment was rinsed forward with THF (2×5 kg). The solution was maintained at −10 to −5° C. for a period of 1 to 3 hours, then cooled to −25 to −20° C.

The acrylate solution in the reactor was transferred to this reactor while maintaining a temperature of −25 to −15° C. The transfer equipment was rinsed forward with THF (8 kg). The suspension was maintained at −25 to −20° C. for a period of 30 to 60 minutes.

Benzyl bromide (32.0 kg) was charged to the reactor over a minimum of 2 hours while maintaining a temperature of −25 to −20° C. The transfer equipment was rinsed forward with THF (8 kg). The mixture was maintained at −25 to −20° C. for a minimum of 16 hours.

A portable storage tank was charged with water (61 L) and hydrochloric acid, 31% (18.1 kg), and then agitated for a minimum of two minutes to form a solution. A second portable storage tank was charged with water (61 L) and hydrochloric acid, 31% (18.1 kg), and then agitated for a minimum of two minutes to form a solution. Both acid solutions were transferred to the reactor over a minimum of two hours while maintaining a temperature of −25 to −15° C. The solution was warmed to 20 to 25° C. over a minimum of three hours.

A portable storage tank was charged with water (29 L) and sodium hydroxide, 50% (4.9 kg). The transfer equipment was rinsed forward with water (15 L) and the mixture was agitated for a minimum of two minutes to form a solution.

The basic solution (29 kg) was transferred to the reactor while maintaining a temperature of 20 to 25° C. until a pH of 9.0 to 9.5 was obtained. The biphasic solution was separated and the aqueous solution was transferred to the 600 L reactor.

The aqueous solution was washed with heptanes (26 kg). The resulting organic solution was transferred to the 1500 L reactor and the transfer equipment was rinsed forward with heptanes (17 kg). The solution was cooled to −30 to −20° C.

A reactor was charged with methanol (113 kg) and cooled to −30 to −20° C. Hydrogen chloride gas (14.4 kg) was charged to the reactor while maintaining a temperature of −30 to −10° C.

The acid solution was charged to above reactor while maintaining a temperature of −30 to −5° C. The transfer equipment was rinsed forward with methanol (19 kg). The solution temperature was adjusted to −10 to −5° C. The solution was reduced to a concentrate volume of 168 to 216 L via vacuum distillation.

The solution was transferred to the 600 L reactor and rinsed forward with methanol (48 kg). The solution was cooled to −10 to −5° C. and reduced to a concentrate volume of 48 to 68 L via vacuum distillation.

Methanol (77 kg) was charged to the 1500 L reactor and rinsed into the reactor. The solution was then cooled to −10 to −5° C. and reduced to a concentrate volume of 48 to 68 L via vacuum distillation.

Methanol (106 kg) was charged to the reactor at a temperature of 30° C. or less, and then heated to 40 to 45° C. The solution was maintained at 40 to 45° C. for a period of 1 to 2 hours. The solution was cooled to 20 to 25° C. over a minimum of 3 hours and maintained in the range for a minimum of 1 hour. The solution was cooled to 2 to 7° C. over a minimum of 1 hour and maintained in the range for a minimum of 1 hour.

The crude product, compound 6, was isolated by filtration, washed with cold methanol (2×15 kg), and tested for purity. The filtrate was kept for further processing.

A reactor was charged with the wet filter cake and methanol (60 kg). The mixture was heated to reflux and maintained at reflux for a period of 1 to 2 hours. The solution was cooled to 2 to 7° C. over a minimum of 4 hours and maintained in the range for a minimum of 1 hour.

The crude product was isolated by filtration, washed with cold methanol (2×15 kg), and tested for purity. The filtrate was kept for further processing.

The reactor was charged with the wet filter cake and methanol (60 kg). The mixture was heated to reflux and maintained at reflux for a minimum of 1 hour. The solution was cooled to 2 to 7° C. over a minimum of 4 hours and maintained in the range for a minimum of 1 hour.

The crude product was isolated by filtration, washed with cold methanol (2×15 kg), and tested for purity and chiral HPLC The reactor was charged with the wet filter cake and methanol (60 kg). The mixture was heated to reflux and maintained at reflux for a minimum of 1 hour. The solution was cooled to 2 to 7° C. over a minimum of 4 hours and maintained in the range for a minimum of 1 hour.

The product compound 6 was isolated by filtration, washed with cold methanol (2×15 kg), sampled for HPLC purity, Chiral HPLC, and isomers and packaged. The packaged product was sampled, tested: HPLC purity; >99.0% a/a and Chiral HPLC, 3.0% and released before use in the next step.

Synthesis of (αS,3R,4R)-4-(3-hydroxyphenyl)-3,4-dimethyl-α-(phenylmethyl)-1-piperidinepropanoic acid monohydrate (Compound 7)

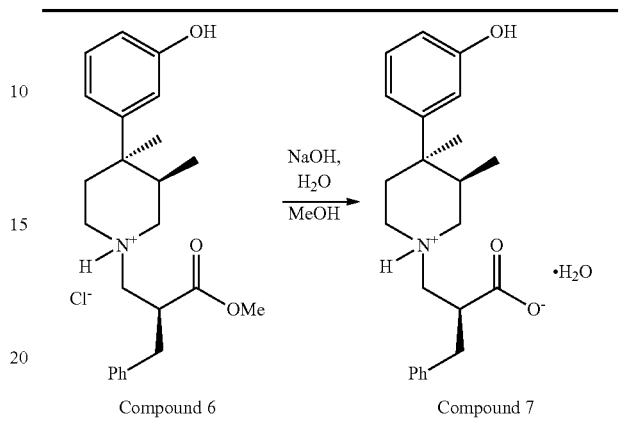

| Reagent | MW | Amount (kg) | Kilomoles | Molar Ratio |
|---|---|---|---|---|
| Compound 6 | 417.97 | 9.9 | 0.02369 | 1.00 |
| Methanol | 32.04 | 107 | — | — |
| Hydrochloric acid, 31% | 36.46 | 9.4 | 0.07992 | 3.37 |
| Sodium hydroxide, 50% w/w | 40.0 | 7.9 | 0.09875 | 4.16 |
| Water | 18.02 | ~244 | — | — |

A reactor was charged with compound 6 (9.9 kg) and water (74 L). The mixture was adjusted to 20 to 25° C.

Sodium hydroxide, 50% (7.9 kg) was charged to the reactor over a minimum of 10 minutes. The transfer equipment was rinsed forward with water (10 L). The pH of the mixture was checked to ensure it was above 12.

The solution was maintained and agitated at a temperature of 20 to 25° C. for a minimum of 4 hours. The reaction mixture was then filtered into a reactor for clarification. The product was rinsed forward with water (8 L).

Methanol (84 kg) was charged to the reactor and adjusted to 20 to 25° C.

Hydrochloric acid, 31% (6.9 kg) was charged to the reactor in portions until a pH of 9.0 to 10.0 was reached.

A new PE drum was charged with water (7.6 L) and hydrochloric acid, 31% (2.5 kg). The transfer equipment was rinsed forward with water (4.0 L) and the solution was agitated for a minimum of two minutes to mix.

A beaker was charged with methanol (0.4 kg), water (0.5 L), and Compound 7 (100 g). The mixture was charged to the reactor and rinsed forward with a solution of water (0.3 L) and methanol (0.2 kg) to seed the reaction mixture.

The pH of the reaction mixture was adjusted with the prepared acidic solution (10.4 kg) until a pH of 5.8 to 6.2 was obtained. The mixture was maintained at 20 to 25° C. for a minimum of 1 hour and verified to ensure crystallization has occurred. The suspension was cooled to 0 to 5° C. and reduced to a concentrate volume of 107 to 124 L via vacuum distillation. The suspension was adjusted to 20 to 25° C. and the pH was checked to ensure it was between 5.8 and 6.2.

The suspension was cooled to 2 to 7° C. and agitated for a minimum of 4 hours.

The product was isolated by filtration, washed with cold water (2×30 L), dried, sampled for water content and packaged. The packaged product was sampled, tested: HPLC purity, 98.% a/a, Chiral HPLC, 98%, and HPLC assay, 98.0% w/w and released prior to use in the next step.

Synthesis of [[2(S)-[[4(R)-(3-hydroxyphenyl)-3(R), 4-dimethyl-1-piperidinyl]methyl]-1-oxo-3-phenyl-propyl]amino]acetic acid dihydrate (Alvimopan)

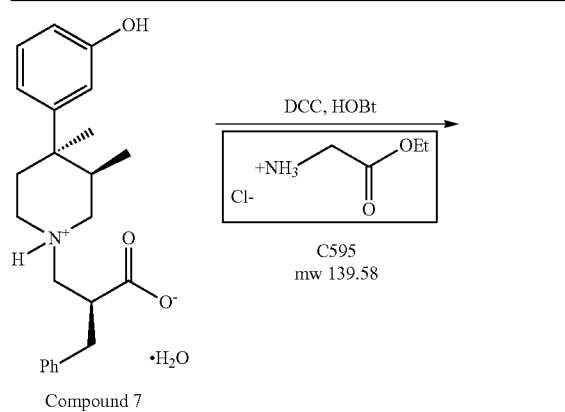

Compound 7

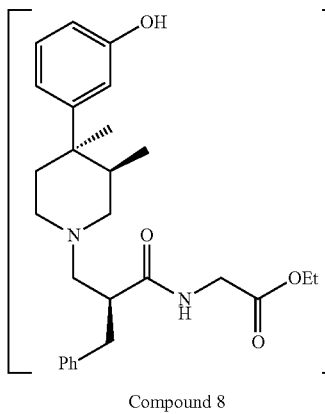

Compound 8

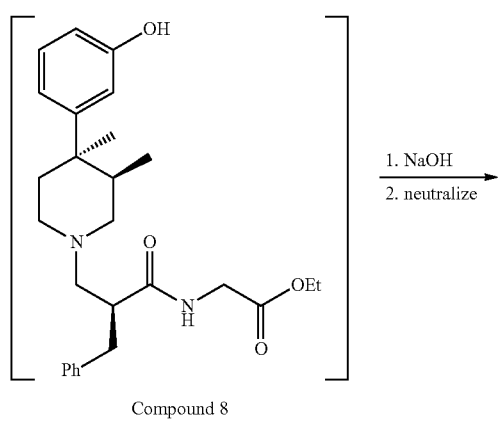

Compound 8

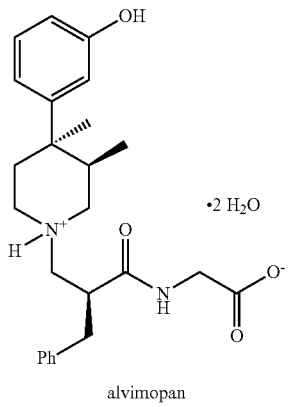 [SMILES: C[C@H]1C[NH+](C[C@H](Cc2ccccc2)C(=O)NCC(=O)[O-])CC[C@@]1(C)c1cccc(O)c1]

alvimopan

| Reagent | MW | Amount (kg) | Kilomoles | Molar Ratio |
|---|---|---|---|---|
| Compound 7 | 385.5 | 7.9 | 2.02049 | 1.00 |
| Glycine ethyl ester hydrochloride | 139.58 | 3.1 | 0.02254 | 1.10 |
| 1-Hydroxybenzotriazole hydrate | 135.13 | 3.5 | 0.02562 | 1.25 |
| Triethylamine | 101.2 | 2.3 | 0.02254 | 1.10 |
| 1,3-Dicyclohexylcarbodiimide | 206.33 | 4.7 | 0.02254 | 1.10 |
| Tetrahydrofuran | 72.11 | 156 | — | — |
| Ethyl acetate | 88.11 | 858 | — | — |
| Soda ash (Sodium carbonate) | 105.99 | 4.8 | — | — |
| Sodium bicarbonate | 84.00 | 3.1 | — | — |
| Brine | — | 112 | — | — |
| Ethanol 1X | 46.07 | 743 | — | — |
| Purified water | 18.02 | 1196 | — | — |
| Sodium hydroxide, 50% w/w | 40.0 | 16.8 | — | — |
| Hydrochloric acid, 31% | 36.46 | 30.0 | — | — |

A portable agitation stainless steel tank (PAST) was charged with tetrahydrofuran (15 kg) and 1,3-dicyclohexyl-carbodiimide (4.7 kg). The transfer equipment was rinsed forward with THF (16 kg).

A reactor was charged with compound 7 (7.9 kg), glycine ethyl ester hydrochloride (3.1 kg), 1-hydroxybenzotriazole hydrate (3.5 kg), tetrahydrofuran (99 kg) and purified water (3.3 kg). With 60% agitation, the mixture was adjusted to 20 to 25° C.

Triethylamine (2.3 kg) was charged to the reactor. The transfer equipment was rinsed forward with tetrahydrofuran (3 kg). The solution was maintained at 20 to 25° C. for a period of 20 to 60 minutes.

The 1,3-dicyclohexylcarbodiimide solution was transferred to the reactor while maintaining a temperature of 20 to 25° C. The transfer equipment was rinsed forward with tetrahydrofuran (23 kg).

The reaction mixture was maintained at 20 to 25° C. for a period of 36 to 38 hours with 100% agitation.

The reaction mixture was cooled to 0 to 5° C. The mixture was maintained in range for a period of 1 to 2 hours then filtered into another reactor. The reaction mixture was rinsed forward with ethyl acetate (20 kg). The mixture was cooled to 0 to 5° C. and reduced to a concentrate volume of 140 to 149 L via vacuum distillation.

Ethyl acetate (731 kg) was charged to the reactor and cooled to 0 to 5° C. The solution was reduced to a concentrate volume of 140 to 149 L via vacuum distillation. The mixture was verified for residual tetrahydrofuran.

A portable agitation stainless steel tank was charged with purified water (94 kg), soda ash (4.8 kg) and sodium bicarbonate (3.1 kg). The mixture was agitated for a minimum of two minutes until the solids dissolved.

The basic solution was charged to the reactor and the temperature was adjusted to 20 to 25° C. The agitation was maintained at 60% for a period of 20 to 60 minutes. The pH of the solution was checked to ensure it was between 9.5 and 10, and adjusted as necessary. The biphasic solution was separated and the organic solution was washed with brine (112 kg).

The reactor was charged with ethyl acetate (87 kg) and cooled to 0 to 5° C. The solution was reduced to a concentrate volume of 140 to 149 L via vacuum distillation, and cooled to −25 to −20° C. The temperature was maintained for a period of 10 to 11 hours.

The suspension was filtered into a reactor, rinsed forward with ethyl acetate (20 kg) and warmed to 0 to 5° C. The filtrate was reduced to a concentrate volume of 39 to 51 L via vacuum distillation.

Ethanol 1X (199 kg) was charged to the reactor and cooled to 0 to 5° C. The solution was reduced to a concentrate volume of 136 to 161 L via vacuum distillation. The reactor was charged with ethanol 1X (93 kg) and the mixture was verified for residual ethyl acetate.

A portable storage tank was charged with purified water (83 kg) and sodium hydroxide, 50% (5.6 kg). The transfer equipment was rinsed forward with purified water (19 kg). The mixture was agitated for a minimum of two minutes to form a solution. The basic solution was transferred to the reactor and maintained at 20 to 25° C. for a period of 1.5 to 3.5 hours. The suspension was filtered into a reactor and adjusted to 20 to 25° C. The 600 L reactor was rinsed forward with purified water (13 kg).

A portable storage tank was charged with purified water (15 kg) and hydrochloric acid, 31% (11.2 kg). The transfer equipment was rinsed forward with purified water (5 kg). The mixture was agitated for a minimum of two minutes to form a solution. The acidic solution was charged to the reactor in portions until a pH of 5.8 to 6.2 was achieved.

The crude product was isolated by filtration, washed with purified water (2×26 kg), washed with ethanol 1X (13 kg), dried and packaged.

The crude product was charged to a reactor with purified water (as per calculation).

A new PE pail was charged with purified water (1.9 kg) and sodium hydroxide, 50% (5.3 kg). The transfer equipment was rinsed forward with purified water (1.0 kg). The mixture was agitated for a minimum of two minutes to form a solution.

The reaction mixture was adjusted to a minimum pH of 13 using the basic solution (7.5 kg). The mixture was maintained at 20 to 25° C. for a period of 20 to 60 minutes.

The mixture was filtered for clarification into a reactor. The reactor was rinsed forward with purified water (10 kg) and was charged with ethanol 1X (as per calculation).

A portable storage tank was charged with purified water (14 kg) and hydrochloric acid, 31% (9.6 kg). The transfer equipment was rinsed forward with purified water (4 kg). The mixture was agitated for a minimum of two minutes to form a solution. The acidic solution was charged to the reactor in portions until a pH of 4.0 to 4.5 was obtained.

A new PE pail was charged with purified water (1.9 kg) and sodium hydroxide, 50% (0.3 kg). The transfer equipment was rinsed forward with purified water (1.0 kg). The mixture was agitated for a minimum of two minutes to form a solution. The basic solution was charged to the reactor in portions until a pH of 5.8 to 6.2 was obtained.

The mixture was verified for the presence of solids and the suspension was maintained at 20 to 25° C. for a minimum of 12 hours.

The product was isolated by filtration, washed first with purified water (as per calculation), next with ethanol 1X (as per calculation) and washed again with purified water (as per calculation). The filter cake was dried and packaged.

The crude product was charged to a reactor with purified water (as per calculation).

A new PE pail was charged with purified water (1.9 kg) and sodium hydroxide, 50% (5.3 kg). The transfer equipment was rinsed forward with purified water (1.0 kg). The mixture was agitated for a minimum of two minutes to form a solution. The basic solution was charged to the reactor in portions until a minimum pH of 13 was obtained.

The mixture was agitated at 20 to 25° C. for a period of 20 to 60 minutes. The mixture was filtered for clarification into another reactor. The reactor was rinsed forward with purified water (10 kg). The reactor was charged with ethanol 1X (as per calculation).

A portable storage tank was charged with purified water (13.5 kg) and hydrochloric acid, 31% (9.2 kg). The transfer equipment was rinsed forward with purified water (3.9 kg). The mixture was agitated for a minimum of two minutes to form a solution. The acidic solution was charged to the reactor in portions until a pH of 4.0 to 4.5 was obtained.

A new PE pail was charged with purified water (1.9 kg) and sodium hydroxide, 50% (0.3 kg). The transfer equipment was rinsed forward with purified water (1.0 kg). The mixture was agitated for a minimum of two minutes to form a solution. The basic solution was charged to the reactor in portions until a pH of 5.8 to 6.2 was obtained.

The mixture was verified for the presence of solids and the suspension was maintained at 20 to 25° C. for a minimum of 12 hours.

The product was isolated by filtration, washed first with purified water (as per calculation), next with ethanol 1X (as per calculation) and washed again with purified water (as per calculation). The filter cake was sampled for chloride, dried and packaged.

The dryer was charged with the over-dried product and purified water (2.0 kg), flushed with nitrogen and left at room temperature until the specified hydration level was achieved.

The hydrated product was then packaged and charged to a 50 L product blender. The product was blended for a period of twenty to thirty minutes and sampled for dryness. The product was blended for a further twenty to thirty minutes and resampled.

The alvimopan was then packaged, sampled, tested: HPLC purity, not less than 99.2% w/w; Chiral HPLC, not less than 99.0%; HPLC assay, 98.0 to 102.0% w/w and Residual solvents, not more than 1.2% w/w total and released.

Example 2

Evaluation of Injectable Formulations (Ability to Formulate and Stability Testing)

Preparation of Formulations for Injection containing Alvimopan

Alvimopan is [[(2S)-2-[[(3R,4R)-4-(3-hydroxyphenyl)-3,4-dimethylpiperidin-1-yl]methyl]-1-oxo-3-phenylpropyl]amino]acetic acid dihydrate. It was used in its native hydrous, form. All weight measurements and concentrations of alvimopan are expressed on an anhydrous basis.

Four product formulations were compounded in 100 ml batches:

| Formulation | Description |
|---|---|
| 1 COMPARATIVE | Alvimopan (1 mg/mL) in 2% glycine (bulking agent), pH 10.5, adjusted with 10N and 1N sodium hydroxide |
| 2 COMPARATIVE | Alvimopan (1 mg/mL) in 5% sodium carbonate (buffer), pH 10.5, adjusted with 1N hydrochloric acid |
| 3 | Alvimopan (1 mg/mL) in 3% mannitol (bulking agent) with 50 mM sodium carbonate (buffer), pH 10.5, adjusted with 1N hydrochloric acid |
| 4 COMPARATIVE | Alvimopan (1 mg/mL) in 3% mannitol (bulking agent) with 50 mM boric acid (buffer), pH 10.5, adjusted with 10N and 1N sodium hydroxide |

The buffers and bulking agents were added to 80% of the final solution volume and the pH was adjusted to pH 10.5 prior to the addition of the active ingredient (alvimopan). The solution was then readjusted to pH 10.5 and mixed to a clear solution. The solution was then brought to the final volume and the pH adjusted with 1 N sodium hydroxide to pH 10.5. The final solutions were sterile filtered. Aliquots of 12.5 mL were dispensed into vials, stoppers seated then placed on the freeze dryer shelf for drying. Formulations 1 to 4 were then lyophilized while simultaneously annealing the formulations, as follows:

| Step | Temperature/Pressure | Time |
|---|---|---|
| 1 | Set to 5° C. ± 3° C. | |
| 2 | Soak at 5° C. ± 3° C. | 60 minutes minimum |
| 3 | Ramp shelf temperature to −40° C. ± 3° C. | Over approximately 90 minutes |
| 4 | Hold at −40° C. ± 3° C. | Approximately 120 minutes |
| 5 | Ramp shelf temperature to −20° C. ± 3° C. | Over approximately 60 minutes |
| 6 | Hold at −20° C. ± 3° C. | Approximately 120 minutes |
| 7 | Ramp shelf temperature to −40° C. ± 3° C. | Over approximately 60 minutes |
| 8 | Hold at −40° C. ± 3° C. | Approximately 120 minutes |
| 9 | Chill condenser to −50° C. or colder and evacuate chamber | |
| 10 | Control vacuum at 100 ± 10 microns with a nitrogen sweep | |
| 11 | Ramp shelf temperature to −15° C. ± 3° C. | Over approximately 50 minutes |
| 12 | Hold at −15° C. ± 3° C. | Approximately 3000 minutes |
| 13 | Ramp shelf temperature to 30° C. ± 3° C. | Over approximately 90 minutes |
| 14 | At end of cycle, slowly restore chamber to 11 ± 0.5 pounds/square inch with nitrogen N.F. filtered through sterilizing microbial retentive filter | |
| 15 | Collapse shelves to seat stoppers | |
| 16 | Restore chamber to ambient pressure | |

The results of the lyophilization and annealing are shown below:

| Formulation | Results |
|---|---|
| 1 COMPARATIVE | Severely melted product |
| 2 COMPARATIVE | Uniform cakes but slight turbidity upon reconstitution in water |
| 3 | Uniform cakes of approximate fill volume and uniform white color; reconstitution with 12.2 mL water for injection or sodium chloride for injection resulted in a clear, colorless solution free from particles upon visual observation (pH was 10.6-10.7 after reconstitution) |
| 4 COMPARATIVE | Collapsed and shrunken cakes |

Formulation 3 resulted in a freeze-dried product that appeared physically stable and readily reconstituted in water or sodium chloride for injection at 1 mg/mL.

Example 3

Bioavailability Testing

The following formulations containing alvimopan were prepared to compare bioavailability of the various dosage forms (oral capsule, oral solution, and intravenous).

Oral Capsules

Oral capsules (6 mg) contained a uniformly dispersed suspension of alvimopan in polyethylene glycol (PEG; molecular weight 3350). Based on certificate of analysis, the actual content of the capsules was assayed at 5.868 mg (97.8%) of 6 mg.

Oral Solution

Oral solution contained alvimopan, propylene glycol (USP), orange drink mix, and purified water (USP). The unit dose oral solution, containing 12 mg alvimopan per 50 mL (0.24 mg/mL). Based on certificate of analysis, the actual content of the oral solution was assayed at 11.868 mg (98.9%) of 12 mg.

Intravenous Formulation

The formulation for injection was formulated as a lyophilized powder containing 12.5 mg of alvimopan (solvent free, anhydrous base) with mannitol, USP, and sodium carbonate anhydrous (NG). Sodium hydroxide (NF) and hydrochloric (NF) were used for pH adjustment prior to freeze-drying to form the lyophilized powder. After the addition of 12.2 ml sodium chloride for injection to the lyophilized powder, the reconstituted solution contained 1 mg/mL. The product was stored in 12 mg vials. Based on certificate of analysis, the actual content of the intravenous formulation was assayed at 11.928 mg (99.4%) of 12 mg.

The bioavailability was evaluated during a three period, crossover study of the relative bioavailability of alvimopan from an oral capsule formulation versus an oral solution, and the absolute bioavailability of alvimopan from the oral capsule compared to the intravenous formulation.

Thirty six subjects were stratified to obtain an equal number of male and female subjects in each sequence and approximately equal numbers by gender in the study. Subjects received a single dose of alvimopan on three separate occasions (Day 1 of each of three periods), with a minimum 14-day washout, which started from the day of dosing of each period. Each subject received a single 12 mg oral capsule dose (2×6 mg capsule), a single 12 mg oral solution dose, and a single 12 mg intravenous dose during each of the three periods (one formulation in each period). Each period consisted of a single dose of alvimopan and 5 days of study assessments. The order in which the subjects received each single dose formulation was determined by the treatment sequence to which the subject was randomized. One of six treatment sequences was possible as determined by the randomization schedule.

Subjects had nothing by mouth (NPO) for at least 10 hours prior to each administration of study medication and remained NPO for 1 hour following study medication administration. Blood samples for pharmacokinetic analysis of alvimopan were collected prior to each administration of study medication and at specified time points during the 96-hour period following study medication administration, depending on whether an oral dose (i.e., capsule or oral solution) or intravenous formulation was administered. A total of approximately 460 mL blood was obtained from each subject over the course of the study. For each period, subjects were confined to the clinical facility until after all Day 3 procedures were completed. Subjects were then required to return to the clinical facility on Days 4 and 5 for the 72-hour and 96-hour blood sample collections, respectively.

Sample Collection

Blood samples (7 mL) were drawn into a tube containing sodium heparin at the following times relative to dosing with oral formulations: 0 hour (within 15 minutes prior to dosing) and at 0.5, 1, 1.5, 2, 3, 4, 6, 9, 12, 18, 24, 36, 48, 72, and 96 hours after dosing. For intravenous solution, in addition to those samples obtained above, four additional samples were drawn at 0.2 hours (at the end of the infusion), 0.25, 0.33, and 0.75 hours after the start of the infusion. Immediately following collection of each sample, each tube was gently inverted and placed in ice. Within 30 minutes of sample collection, the tubes were centrifuged at about 1200×g for 15 minutes at approximately 5° C. in order to separate the cells from the plasma. No aids for separation were used. The plasma was transferred with clean pipettes and placed in two polypropylene storage tubes in equal volumes. The storage tubes were labeled with the following information: protocol number, subject number, period number, relative time of sample, and analyte. The label was taped with clear tape to assure adherence of the label. The storage tubes were placed in a freezer at 70° C. or below until shipment. The samples were sent frozen to the analytical facility and kept frozen until the time of analysis.

Bioanalytical Methodology

Plasma samples were assayed for alvimopan concentrations using a validated and sensitive LC/MS/MS (liquid chromatography/mass spectrometry/mass spectrometry) method. The assay used a solid phase extraction process to extract alvimopan, its metabolite, and the internal standard from plasma. The solvent was evaporated, and the residue was dissolved in a solvent, a portion of which was injected in an liquid chromatography system. Detection was by MS/MS (mass spectrometry/mass spectrometry) by the use of a SCIEX API 3000® mass spectrometer. Calibration curves and quality control samples were included in each run. The ranges of the assay for both analytes were from 0.25 ng/mL to 250 ng/mL, and the limit of quantification for both analytes was 0.25 ng/mL. Quality control standards at three concentrations were included in each analytical run (low, 0.75 ng/mL; middle, 25 ng/mL; and high, 175 ng/mL). Due to the high concentrations from the intravenous solution, another standard was added (800 ng/mL). The intra assay precision, expressed as a coefficient of variation (% CV), for the lower quality control standard was 12.9% for alvimopan; and the inter assay accuracy, expressed as a % deviation of the mean from the theoretical (% DMT), was 1.2% for alvimopan.

Pharmacokinetic Measurements

Alvimopan concentrations in plasma were entered into a spreadsheet. After adaptation of the spreadsheet data for compatibility as an entry file, the information was processed with WinNonlin® Professional (Version 3.3) to obtain pharmacokinetic variables and to produce concentration-time plots and tables. The WinNonlin program was validated using the WinNonlin Validation Kit (Version 3.3). The pharmacokinetic variables for alvimopan during the oral treatments were obtained using the noncompartmental Model 200 with extravascular input. Plasma concentrations of alvimopan after intravenous administration were analyzed using the noncompartmental Model 202 with a constant rate of infusion. Infusion time was entered as 12 minutes for all subjects.

Nominal sampling times were used for pharmacokinetic analyses of alvimopan; any deviations of the sampling times from the scheduled times were not considered significant. Concentration values that were reported as below the limit of quantification (BLQ) were treated as 0 for computing mean concentrations and in the concentration-time graphs.

For pharmacokinetic analyses of alvimopan, BLQ results were included in the input file. Concentrations in plasma were used as reported; but measurable concentrations observed after obtaining a BLQ result were excluded from analysis.

The following pharmacokinetic parameters were obtained for alvimopan from WinNonlin output files:

| | |
|---|---|
| Cmax | maximum observed plasma drug concentration |
| $C_p$ | plasma drug concentration at specified time point |
| Tmax | time to maximum plasma drug concentration, obtained directly from concentration-time data |
| $t\frac{1}{2}\lambda z$ | half-life of the terminal portion of the disposition phase |
| AUC(0-tlast) | area under the plasma drug concentration-time curve from time 0 to the time of the last measurable concentration |
| AUC(0-∞) | area under the plasma drug concentration-time curve from time 0 to infinity |
| CL | total body plasma clearance (in mL/min and mL/min/kg), for I.V. formulation only |
| Vss | apparent volume of distribution at steady-state (in L and L/kg), for I.V. formulation only |
| CL/F | apparent oral clearance (in mL/min and mL/min/kg), for oral formulations |
| Vz/F | apparent oral volume of distribution (in L and L/kg), for oral formulations |
| Vz | apparent volume of distribution during the terminal exponential phase (in L and L/kg), for I.V. formulation only |
| $CL_\beta$ | blood clearance (in mL/min), for I.V. formulation only |
| Tlag | time from 0 hour to the time of the first measurable concentration |
| clinically relevant $t_{1/2\beta}$ | half-life of the disposition phase of the clinically relevant portion of the plasma drug concentration-time profile based on manually selected time points representing the first disposition phase (see below) |
| AUC(0-∞)' | area under the plasma drug concentration-time curve from time 0 to infinity describing the clinically relevant portion of the plasma drug concentration-time curve |
| AUC ratio | AUC(0-∞)'/AUC(0-∞) |

To calculate the clinically relevant $t_{1/2\beta}$, a second noncompartmental modeling of data was performed with WinNonlin using manually selected ranges for the estimation of $\lambda z$. Ranges were selected by identifying time points that were not part of a second and longer disposition phase. To determine whether this second modeling was relevant, the ratio of AUC (0-∞)'/AUC(0-∞) was calculated from the Day 1 data for alvimopan. If the mean value of the ratio was ≥85%, then the AUC(0-∞)' was considered to be the clinically relevant portion of AUC(0-∞). The clinically relevant $t_{1/2\beta}$ was based on this second modeling using manually selected ranges as well.

For determinations of relative and absolute bioavailability, specific AUC ratios were computed. For relative bioavailability purposes, the oral capsule was considered as the Test and the oral solution as the Reference. For absolute bioavailability, the orally administered formulations were considered as the Test and the I.V. formulation as the Reference. The AUC ratios (and 95% confidence intervals) were calculated with both AUC(0-$t_{last}$) and AUC(0-∞). Primary consideration was given to AUC(0-∞). The computations originated from the least squared mean (LS Mean) from the analysis of variance (ANOVA). The LS Mean difference for two comparative treatments was then converted to the original scale to obtain bioavailability ratios. The following ratios were calculated for determination of relative and absolute bioavailability:

Relative bioavailability: oral capsule (test) vs. oral solution (reference)

Absolute bioavailability: oral capsule (test) vs. I.V. formulation (reference)

oral solution (test) vs. I.V. formulation (reference)

$$\frac{AUC(0-\infty) \text{ Test}}{AUC(0-\infty) \text{ Reference}}$$

$$\frac{AUC(0-t_{last}) \text{ Test}}{AUC(0-t_{last}) \text{ Reference}}$$

The total blood clearance ($CL_\beta$) was calculated following intravenous administration using the following equation:

$$CL_B = CL^*(C_p/C_\beta)$$

where:
CL was the geometric mean CL (ml/min) following I.V. administration and the $C_p/C_\beta$ was the reciprocal for the blood: plasma distribution ratio of 0.68 (i.e., $C_p=1$; $C_\beta=0.68$).

The results are shown in the following table:

Summary of Pharmacokinetic Parameters for Alvimopan after a Single Dose of Oral Capsule Alvimopan 12 mg (2×6 mg capsules), a Single Dose of Oral Solution Containing Alvimopan 12 mg (0.24 mg/mL), and a Single Dose of Intravenous Formulation Containing Alvimopan 12 mg (1 mg/mL)

| Parameter | Alvimopan 12 mg | | |
|---|---|---|---|
| | Oral Capsule N = 30 | Oral Solution N = 30 | I.V. Formulation N = 30 |
| Cmax (ng/mL) | | | |
| Mean ± SD | 9.49 ± 5.72 | 21.81 ± 9.99 | 1017 ± 275 |
| (% CV) | (60.2) | (45.8) | (27.0) |
| Geometric Mean | 7.66 | 19.99 | 981 |
| Tmax (hr) | | | |
| Mean ± SD | 2.0 ± 0.7 | 1.4 ± 0.6 | 0.2 ± 0.0 |
| (% CV) | (35.2) | (45.5) | (7.4) |
| Geometric Mean | 1.8 | 1.3 | 0.2 |
| Median | 2.0 | 1.0 | 0.2 |
| (Minimum, Maximum) | (1.0, 4.0) | (0.5, 3.0) | (0.2, 0.25) |
| $t^{1/2}\lambda z$ (hr) | | | |
| Mean ± SD | 6.2 ± 6.7 | 5.5 ± 4.4 | 5.3 ± 3.8 |
| (% CV) | (108.5) | (81.0) | (72.5) |
| Geometric Mean | 3.9 | 4.4 | 4.2 |
| Clinically Relevant $t^{1/2}$ (hr) | | | |
| Mean ± SD | 1.6 ± 0.6 | 1.7 ± 0.7 | 3.0 ± 2.3 |
| (% CV) | (39.6) | (38.4) | (79.0) |
| Geometric Mean | 1.5 | 1.6 | 2.4 |
| AUC(0-tlast) (hr*ng/mL) | | | |
| Mean ± SD | 34.3 ± 19.7 | 77.7 ± 35.3 | 520.0 ± 121.9 |
| (% CV) | (57.5) | (45.4) | (23.5) |
| Geometric Mean | 27.3 | 70.5 | 507.1 |
| AUC(0-∞) (hr*ng/mL) | | | |
| Mean ± SD | 37.4 ± 21.2 | 80.7 ± 36.7 | 522.5 ± 122.4 |
| (% CV) | (56.6) | (45.5) | (23.4) |
| Geometric Mean | 30.2 | 73.2 | 509.5 |
| Vss (L) | | | |
| Mean ± SD | — | — | 30 ± 10 |
| (% CV) | | | (34.4) |
| Geometric Mean | | | 29 |
| Vss (L/kg)[a] | | | |
| Mean ± SD | — | — | 0.43 ± 0.19 |
| (% CV) | | | (43.5) |
| Geometric Mean | | | 0.40 |
| Vz (L) | | | |
| Mean ± SD | — | — | 173 ± 122 |
| (% CV) | | | (70.5) |
| Geometric Mean | | | 143 |
| Vz (L/kg)[a] | | | |
| Mean ± SD | — | — | 2.51 ± 2.11 |
| (% CV) | | | (84.0) |
| Geometric Mean | | | 1.99 |
| Vz/F (L) | | | |
| Mean ± SD | 3071 ± 2813 | 1219 ± 771 | — |
| (% CV) | (91.6) | (63.3) | |
| Geometric Mean | 2226 | 1031 | |
| CL (mL/min) | | | |
| Mean ± SD | — | — | 402 ± 89 |
| (% CV) | | | (22.1) |
| Geometric Mean | | | 393 |
| CL (mL/min/kg)[a] | | | |
| Mean ± SD | — | — | 5.62 ± 1.30 |
| (% CV) | | | (23.2) |
| Geometric Mean | | | 5.47 |
| CL/F (mL/min) | | | |
| Mean ± SD | 8809 ± 7579 | 3014 ± 1423 | — |
| (% CV) | (86.0) | (47.2) | |
| Geometric Mean | 6614 | 2731 | |

[a]Values are normalized for body weight.

The absolute bioavailabilities of alvimopan from oral capsule and oral solution were 6.0% (95% confidence intervals: 4.7-7.7%) and 14.3% (95% confidence interval: 11.1-18.3%), respectively. The bioavailability of alvimopan capsule relative to oral solution was 41.9% (95% confidence interval: 32.6-53.7%). The intravenous formulation of alvimopan produced six times and 14 times higher systemic exposure than provided by the oral capsule and oral solution, respectively.

When ranges are used herein for physical properties, such as molecular weight, or chemical properties, such as chemical formulae, all combinations and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A composition comprising:
   a. alvimopan or a pharmaceutically-acceptable salt thereof;
   b. at least one sugar alcohol bulking agent, wherein said at least one sugar alcohol is mannitol; and
   c. a bicarbonate or carbonate base.

2. The composition according to claim 1, wherein the composition comprises sodium carbonate anhydrous.

3. The composition of claim 1, wherein the composition is obtained by lyophilizing an aqueous formulation comprising alvimopan or a pharmaceutically acceptable salt thereof, mannitol and a carbonate base selected from sodium carbonate and sodium carbonate anhydrous.

4. The composition of claim 3, wherein the aqueous formulation has a pH in the range of from about 9 to about 11.

5. The solution of claim 4, wherein the pH of the aqueous formulation is about 10.5.

6. An injectable pharmaceutical composition prepared by admixing in a pharmaceutically acceptable solvent:
   a. alvimopan;
   b. mannitol; and
   c. a bicarbonate or carbonate base in an amount sufficient to provide a pH to said composition in the range of from about 9 to about 11.

7. The composition of claim 6, wherein the base is a carbonate base.

8. The composition of claim 7, wherein the base is sodium carbonate or sodium carbonate anhydrous.

9. The composition of claim 6, wherein the solvent is an aqueous solvent.

10. The composition of claim 9, wherein said aqueous solvent is water, isotonic sodium chloride solution, Ringer's solution, dextrose solution or lactated Ringer's solution.

11. A partially or fully dried product, wherein the composition of claim 6 has been dried to remove at least a portion of said solvent.

12. The product of claim 11 that has been lyophilized.

13. A dosage form prepared by:
   a. admixing alvimopan, mannitol and a bicarbonate or carbonate base in a pharmaceutically acceptable aqueous solvent to form a solution;
   b. adjusting pH of said solution in the range of from about 9 to about 11;
   c. lyophilizing said solution to form a partially or fully dried product.

14. The composition of claim 13, wherein the base is a carbonate base.

15. The composition of claim 14, wherein the base is sodium carbonate or sodium carbonate anhydrous.

16. The composition of claim 13, wherein the pH of said solution is adjusted in the range of from about 10 to about 10.5.

17. The composition of claim 16, wherein the pH of said solution is adjusted to about 10.5.

* * * * *